(12) United States Patent
Hoeflich

(10) Patent No.: US 10,463,050 B2
(45) Date of Patent: Nov. 5, 2019

(54) TRICHOME AND PISTIL MATURING FORMULATION

(71) Applicant: Jo Hoeflich, Raymond, ME (US)

(72) Inventor: Jo Hoeflich, Raymond, ME (US)

( * ) Notice: Subject to any disclaimer, the term of this patent is extended or adjusted under 35 U.S.C. 154(b) by 0 days.

(21) Appl. No.: 15/311,783

(22) PCT Filed: Nov. 15, 2016

(86) PCT No.: PCT/US2016/062102
§ 371 (c)(1),
(2) Date: Nov. 16, 2016

(87) PCT Pub. No.: WO2017/087421
PCT Pub. Date: May 26, 2017

(65) Prior Publication Data
US 2017/0325463 A1    Nov. 16, 2017

Related U.S. Application Data

(60) Provisional application No. 62/285,987, filed on Nov. 16, 2015, provisional application No. 62/344,532, filed on Jun. 2, 2016.

(51) Int. Cl.
| | | |
|---|---|---|
| *A01N 65/48* | (2009.01) | |
| *A01N 59/00* | (2006.01) | |
| *A01N 65/20* | (2009.01) | |
| *A01N 65/42* | (2009.01) | |
| *A23B 7/16* | (2006.01) | |
| *A01N 65/08* | (2009.01) | |
| *A01N 65/10* | (2009.01) | |
| *A01N 65/22* | (2009.01) | |
| *A01N 65/24* | (2009.01) | |
| *A01N 65/28* | (2009.01) | |
| *A01N 65/34* | (2009.01) | |
| *A01N 65/38* | (2009.01) | |
| *A01N 65/40* | (2009.01) | |

(52) U.S. Cl.
CPC ............ *A01N 65/48* (2013.01); *A01N 59/00* (2013.01); *A01N 65/08* (2013.01); *A01N 65/10* (2013.01); *A01N 65/20* (2013.01); *A01N 65/22* (2013.01); *A01N 65/24* (2013.01); *A01N 65/28* (2013.01); *A01N 65/34* (2013.01); *A01N 65/38* (2013.01); *A01N 65/40* (2013.01); *A01N 65/42* (2013.01); *A23B 7/16* (2013.01); *A23V 2002/00* (2013.01)

(58) Field of Classification Search
CPC combination set(s) only.
See application file for complete search history.

(56) References Cited

U.S. PATENT DOCUMENTS

| | | | |
|---|---|---|---|
| 3,796,562 A | 3/1974 | Lamont et al. | |
| 5,078,782 A | 1/1992 | Nielsen et al. | |
| 5,227,162 A * | 7/1993 | Ferrari | A01N 65/00 424/703 |
| 5,342,630 A | 8/1994 | Jones | |
| 5,466,459 A | 11/1995 | Wilson | |
| 5,614,203 A | 3/1997 | Dezur et al. | |
| 5,698,191 A | 12/1997 | Wiersma et al. | |
| 5,711,953 A * | 1/1998 | Bassett | A01N 65/00 424/405 |
| 5,756,100 A | 5/1998 | Martinez | |
| 6,231,865 B1 | 5/2001 | Hsu et al. | |
| 6,284,286 B1 | 9/2001 | Arimoto et al. | |
| 6,523,298 B2 | 2/2003 | Neumann | |
| 7,019,036 B2 | 3/2006 | Hiromoto | |
| 7,029,687 B1 | 4/2006 | Joiner | |
| 8,202,557 B1 | 6/2012 | Doty | |
| 8,956,997 B2 | 2/2015 | Cookston | |
| 9,198,435 B2 | 12/2015 | Bailey-Jackson | |
| 2010/0047374 A1 * | 2/2010 | Sakakibara | A61K 31/133 424/780 |
| 2014/0242199 A1 * | 8/2014 | Manhas | A01N 25/02 424/736 |

FOREIGN PATENT DOCUMENTS

JP        08295601        12/1996

* cited by examiner

*Primary Examiner* — John Pak
*Assistant Examiner* — Daniel L Branson
(74) *Attorney, Agent, or Firm* — Preti Flaherty Beliveau & Pachios LLP

(57) ABSTRACT

A trichome and pistil maturing bud finisher plant treatment formula to which plants, pollinators, and humans respond favorably but which deters insects and contagions. The formulas include a series of edible spices claimed in specific ratios. The spices comprise food grade products manufactured for human consumption and specifically comprise Garlic, Ginger, Cinnamon, Turmeric, Clove, Black Pepper, Powdered Ancho Chili, Coriander, Cayenne, Cumin, Fenugreek, Nutmeg, and Oregano. In the bud finisher formula, these spices are mixed with potassium bicarbonate in a first container in relative quantities. Meanwhile, the bud finisher formula requires mixing sesame oil with apple cider vinegar, also in a particular ratio. The bud finisher formula matures pistils and trichomes. An alternative bud shield formula excludes the potassium bicarbonate and apple cider vinegar to also mature trichomes but matures pistils at a slower rate. After dilution the plant treatment formula is applied to all surfaces of the plant.

12 Claims, 10 Drawing Sheets

FIG. 8

Bud Finisher

| Tiers | Ingredients | Scientific Name | CAS# & Compound | | Function | ml | Teaspoons | Percentage | Tier Percentage |
|---|---|---|---|---|---|---|---|---|---|
| 1 | Sesame Oil | Sesamum indicum | 533-31-3 | Sesamol | insecticide, fungicide | 14.79 | 3.00 | 28.71% | 57.43% |
| | Apple Cider Vinegar | Malus sylvestris | 8028-52-2 | Acetic acid | fungicide | 14.79 | 3.00 | 28.71% | |
| 2 | Potassium Bicarbonate | potassium hydrogen carbonate | 298-14-6 | chko3 | fungicide, pistil finisher | 7.39 | 1.50 | 14.36% | 14.36% |
| 3 | Garlic | Allium sativum | 539-86-6 | Allicin | insecticide, fungicide | 2.84 | 0.58 | 5.52% | 16.57% |
| | Ginger | Zingiber officinale | 122-48-5 | Zingerone | fungicide | 2.84 | 0.58 | 5.52% | |
| | Cinnamon | Cinnamomum verum | 104-55-2 | Cinnamaldehyde | insecticide, fungicide | 2.84 | 0.58 | 5.52% | |
| 4 | Turmeric | Curcuma longa | 458-37-7 | Curcumin | insecticide, fungicide | 1.42 | 0.29 | 2.76% | 5.52% |
| | Clove | Syzygium aromaticum | 97-53-0 | Eugenol | insecticide, fungicide | 1.42 | 0.29 | 2.76% | |
| 5 | Black Pepper | Piper nigrum | 94-62-2 | Piperine | insecticide, fungicide | 0.71 | 0.14 | 1.38% | 4.14% |
| | Powdered Ancho Ch | Capsicum annuum | 404-86-4 | Capsaicin | pesticide, bud finisher | 0.71 | 0.14 | 1.38% | |
| | Coriander | Coriandrum sativum | 8008-52-4 | Coriander Oil | insecticide, fungicide | 0.71 | 0.14 | 1.38% | |
| 6 | Cayenne | Capsicum annuum | 404-86-4 | Capsaicin | pesticide, bud finisher | 0.34 | 0.07 | 0.66% | 1.33% |
| | Cumin | Cuminum cyminum | 122-03-2 | Cuminaldehyde | insecticide, fungicide | 0.34 | 0.07 | 0.66% | |
| 7 | Fenugreek | Trigonella foenum-graecum | 535-83-1 | Trigonelline | insecticide, fungicide | 0.17 | 0.03 | 0.33% | 0.33% |
| 8 | Nutmeg | Myristica fragrans | 555-45-3 | Trimyristin | insecticide, fungicide | 0.09 | 0.02 | 0.17% | 0.33% |
| | Oregano | Origanum Vulgare | 499-75-2 | Carvacrol | insecticide, fungicide | 0.09 | 0.02 | 0.17% | |
| Total | | | | | | 51.50 | 10.45 | 100.00% | 100.00% |

FIG. 9

Bud Finisher With Water

| Tiers | Ingredients | Scientific Name | CAS# & Compound | | Function | ml | Teaspoons | Percentage | Tier Percentage |
|---|---|---|---|---|---|---|---|---|---|
| 1 | Sesame Oil | Sesamum indicum | 533-31-3 | Sesamol | insecticide, fungicide | 14.79 | 3.00 | 0.385% | 0.771% |
| | Apple Cider Vinegar | Malus sylvestris | 8028-52-2 | Acetic acid | fungicide | 14.79 | 3.00 | 0.385% | |
| 2 | Potassium Bicarbonate | potassium hydrogen carbonate | 298-14-6 | chko3 | fungicide, pistil finisher | 7.39 | 1.50 | 0.193% | 0.193% |
| 3 | Garlic | Allium sativum | 539-86-6 | Allicin | insecticide, fungicide | 2.84 | 0.58 | 0.074% | 0.222% |
| | Ginger | Zingiber officinale | 122-48-5 | Zingerone | fungicide | 2.84 | 0.58 | 0.074% | |
| | Cinnamon | Cinnamomum verum | 104-55-2 | Cinnamaldehyde | insecticide, fungicide | 2.84 | 0.58 | 0.074% | |
| 4 | Turmeric | Curcuma longa | 458-37-7 | Curcumin | insecticide, fungicide | 1.42 | 0.29 | 0.037% | 0.074% |
| | Clove | Syzygium aromaticum | 97-53-0 | Eugenol | insecticide, fungicide | 1.42 | 0.29 | 0.037% | |
| 5 | Black Pepper | Piper nigrum | 94-62-2 | Piperine | insecticide, fungicide | 0.71 | 0.14 | 0.019% | 0.056% |
| | Powdered Ancho Ch | Capsicum annuum | 404-86-4 | Capsaicin | pesticide, bud finisher | 0.71 | 0.14 | 0.019% | |
| | Coriander | Coriandrum sativum | 8008-52-4 | Coriander Oil | insecticide, fungicide | 0.71 | 0.14 | 0.019% | |
| 6 | Cayenne | Capsicum annuum | 404-86-4 | Capsaicin | pesticide, bud finisher | 0.34 | 0.07 | 0.009% | 0.02% |
| | Cumin | Cuminum cyminum | 122-03-2 | Cuminaldehyde | insecticide, fungicide | 0.34 | 0.07 | 0.009% | |
| 7 | Fenugreek | Trigonella foenum-graecum | 535-83-1 | Trigonelline | insecticide, fungicide | 0.17 | 0.03 | 0.004% | 0.004% |
| 8 | Nutmeg | Myristica fragrans | 555-45-3 | Trimyristin | insecticide, fungicide | 0.09 | 0.02 | 0.002% | 0.004% |
| | Oregano | Origanum Vulgare | 499-75-2 | Carvacrol | insecticide, fungicide | 0.09 | 0.02 | 0.002% | |
| | 1 gallon of water (3.7 Oxidane) | | 7732-18-5 | H2O | Dilution & spreading agent | 3785.41 | 767.99 | 98.66% | 98.66% |
| Total | | | | | | 3836.91 | 778.44 | 100.00% | 100.00% |

FIG. 10

Bud Shield

| Tiers | Ingredients | Scientific Name | CAS# & Compound | | Function | ml | Teaspoons | Percentage | Tier Percentage |
|---|---|---|---|---|---|---|---|---|---|
| 1 | Sesame Oil | Sesamum indicum | 533-31-3 | Sesamol | insecticide, fungicide | 14.79 | 3.00 | 50.44% | 50.44% |
| 2 | Garlic | Allium sativum | 539-86-6 | Allicin | insecticide, fungicide | 2.84 | 0.58 | 9.70% | |
| | Ginger | Zingiber officinale | 122-48-5 | Zingerone | fungicide | 2.84 | 0.58 | 9.70% | |
| | Cinnamon | Cinnamomum verum | 104-55-2 | Cinnamaldehyde | insecticide, fungicide | 2.84 | 0.58 | 9.70% | 29.10% |
| 3 | Turmeric | Curcuma longa | 458-37-7 | Curcumin | insecticide, fungicide | 1.42 | 0.29 | 4.85% | |
| | Clove | Syzygium aromaticum | 97-53-0 | Eugenol | insecticide, fungicide | 1.42 | 0.29 | 4.85% | 9.70% |
| | Black Pepper | Piper nigrum | 94-62-2 | Piperine | insecticide, fungicide | 0.71 | 0.14 | 2.42% | |
| | Powdered Ancho Chili | Capsicum annuum | 404-86-4 | Capsaicin | pesticide, bud finisher | 0.71 | 0.14 | 2.42% | |
| 4 | Coriander | Coriandrum sativum | 8008-52-4 | Coriander Oil | insecticide, fungicide | 0.71 | 0.14 | 2.42% | 7.27% |
| | Cayenne | Capsicum annuum | 404-86-4 | Capsaicin | pesticide, bud finisher | 0.34 | 0.07 | 1.16% | |
| 5 | Cumin | Cuminum cyminum | 122-03-2 | Cuminaldehyde | insecticide, fungicide | 0.34 | 0.07 | 1.16% | 2.33% |
| 6 | Fenugreek | Trigonella foenum-graecum | 535-83-1 | Trigonelline | insecticide, fungicide | 0.17 | 0.03 | 0.58% | 0.58% |
| | Nutmeg | Myristica fragrans | 555-45-3 | Trimyristin | insecticide, fungicide | 0.09 | 0.02 | 0.29% | |
| 7 | Oregano | Origanum Vulgare | 499-75-2 | Carvacrol | insecticide, fungicide | 0.09 | 0.02 | 0.29% | 0.58% |
| Total | | | | | | 29.32 | 5.95 | 100.00% | 100.00% |

FIG. 11

Bud Shield With Water

| Tiers | Ingredients | Scientific Name | CAS# & Compound | | Function | ml | Teaspoons | Percentage | Tier Percentage |
|---|---|---|---|---|---|---|---|---|---|
| 1 | Sesame Oil | Sesamum indicum | 533-31-3 | Sesamol | insecticide, fungicide | 14.79 | 3.00 | 0.388% | 0.388% |
| 2 | Garlic | Allium sativum | 539-86-6 | Allicin | insecticide, fungicide | 2.84 | 0.58 | 0.075% | |
| | Ginger | Zingiber officinale | 122-48-5 | Zingerone | fungicide | 2.84 | 0.58 | 0.075% | |
| | Cinnamon | Cinnamomum verum | 104-55-2 | Cinnamaldehyde | insecticide, fungicide | 2.84 | 0.58 | 0.075% | 0.224% |
| 3 | Turmeric | Curcuma longa | 458-37-7 | Curcumin | insecticide, fungicide | 1.42 | 0.29 | 0.037% | |
| | Clove | Syzygium aromaticum | 97-53-0 | Eugenol | insecticide, fungicide | 1.42 | 0.29 | 0.037% | 0.075% |
| | Black Pepper | Piper nigrum | 94-62-2 | Piperine | insecticide, fungicide | 0.71 | 0.14 | 0.019% | |
| | Powdered Ancho Chili | Capsicum annuum | 404-86-4 | Capsaicin | pesticide, bud finisher | 0.71 | 0.14 | 0.019% | |
| 4 | Coriander | Coriandrum sativum | 8008-52-4 | Coriander Oil | insecticide, fungicide | 0.71 | 0.14 | 0.019% | 0.056% |
| | Cayenne | Capsicum annuum | 404-86-4 | Capsaicin | pesticide, bud finisher | 0.34 | 0.07 | 0.009% | |
| 5 | Cumin | Cuminum cyminum | 122-03-2 | Cuminaldehyde | insecticide, fungicide | 0.34 | 0.07 | 0.009% | 0.018% |
| 6 | Fenugreek | Trigonella foenum-graecum | 535-83-1 | Trigonelline | insecticide, fungicide | 0.17 | 0.03 | 0.004% | 0.004% |
| | Nutmeg | Myristica fragrans | 555-45-3 | Trimyristin | insecticide, fungicide | 0.09 | 0.02 | 0.002% | |
| 7 | Oregano | Origanum Vulgare | 499-75-2 | Carvacrol | insecticide, fungicide | 0.09 | 0.02 | 0.002% | 0.004% |
| | 1 gallon of water (3.75 | Oxidane | 7732-18-5 | H2O | Dilution & spreading | 3785.41 | 767.99 | 99.231% | 99.23% |
| Total | | | | | | 3814.73 | 773.94 | 100.00% | 100.00% |

FIG. 12

MAGIC FLOWER - 3.2

| Tiers | Ingredients | Scientific Name | CAS# & Compound | | Function | ml | Teaspoons | Percentage | Tier Percentage |
|---|---|---|---|---|---|---|---|---|---|
| | Sesame Oil | Sesamum indicum | 533-31-3 | Sesamol | insecticide, fungicide | 14.79 | 3.00 | 28.52% | |
| 1 | Apple Cider Vinegar | Malus sylvestris | 8028-52-2 | Acetic acid | fungicide | 14.79 | 3.00 | 28.52% | 57.05% |
| 2 | Potassium Bicarbonate | potassium hydrogen carbonate | 298-14-6 | chko3 | fungicide, pistil finisher | 7.39 | 1.50 | 14.26% | 14.26% |
| | Garlic | Allium sativum | 539-86-6 | Allicin | insecticide, fungicide | 2.84 | 0.58 | 5.49% | |
| | Ginger | Zingiber officinale | 122-48-5 | Zingerone | fungicide | 2.84 | 0.58 | 5.49% | |
| 3 | Cinnamon | Cinnamomum verum | 104-55-2 | Cinnamaldehyde | insecticide, fungicide | 2.84 | 0.58 | 5.49% | 16.46% |
| | Turmeric | Curcuma longa | 458-37-7 | Curcumin | insecticide, fungicide | 1.42 | 0.29 | 2.74% | |
| 4 | Clove | Syzygium aromaticum | 97-53-0 | Eugenol | insecticide, fungicide | 1.42 | 0.29 | 2.74% | 5.49% |
| 5 | Black Pepper | Piper nigrum | 94-62-2 | Piperine | insecticide, fungicide | 0.71 | 0.14 | 1.37% | 1.37% |
| | Powdered Ancho Chili | Capsicum annuum | 404-86-4 | Capsaicin | pesticide, bud finisher | 0.71 | 0.14 | 1.37% | |
| 6 | Coriander | Coriandrum sativum | 8008-52-4 | Coriander Oil | insecticide, fungicide | 0.71 | 0.14 | 1.37% | 2.74% |
| | Salt | Sodium Chloride | 7647-14-5 | NaCl | Ionic catalyst | 0.34 | 0.07 | 0.66% | |
| | Cayenne | Capsicum annuum | 404-86-4 | Capsaicin | pesticide, bud finisher | 0.34 | 0.07 | 0.66% | |
| 7 | Cumin | Cuminum cyminum | 122-03-2 | Cuminaldehyde | insecticide, fungicide | 0.34 | 0.07 | 0.66% | 1.97% |
| 8 | Fenugreek | Trigonella foenum-graecum | 535-83-1 | Trigonelline | insecticide, fungicide | 0.17 | 0.03 | 0.33% | 0.33% |
| | Nutmeg | Myristica fragrans | 555-45-3 | Trimyristin | insecticide, fungicide | 0.09 | 0.02 | 0.16% | |
| 9 | Oregano | Origanum Vulgare | 499-75-2 | Carvacrol | insecticide, fungicide | 0.09 | 0.02 | 0.16% | 0.33% |
| Total | | | | | | 51.84 | 10.52 | 100.00% | 100.00% |

FIG. 13

MAGIC FLOWER - 3.2

| Tiers | Ingredients | Scientific Name | CAS# & Compound | | Function | ml | Teaspoons | Percentage | Tier Percentage |
|---|---|---|---|---|---|---|---|---|---|
| | Sesame Oil | Sesamum indicum | 533-31-3 | Sesamol | insecticide, fungicide | 14.79 | 3.00 | 0.385% | |
| 1 | Apple Cider Vinegar | Malus sylvestris | 8028-52-2 | Acetic acid | fungicide | 14.79 | 3.00 | 0.385% | 0.771% |
| 2 | Potassium Bicarbonate | potassium hydrogen carbonate | 298-14-6 | chko3 | fungicide, pistil finisher | 7.39 | 1.50 | 0.193% | 0.193% |
| | Garlic | Allium sativum | 539-86-6 | Allicin | insecticide, fungicide | 2.84 | 0.58 | 0.074% | |
| | Ginger | Zingiber officinale | 122-48-5 | Zingerone | fungicide | 2.84 | 0.58 | 0.074% | |
| 3 | Cinnamon | Cinnamomum verum | 104-55-2 | Cinnamaldehyde | insecticide, fungicide | 2.84 | 0.58 | 0.074% | 0.222% |
| | Turmeric | Curcuma longa | 458-37-7 | Curcumin | insecticide, fungicide | 1.42 | 0.29 | 0.037% | |
| 4 | Clove | Syzygium aromaticum | 97-53-0 | Eugenol | insecticide, fungicide | 1.42 | 0.29 | 0.037% | 0.074% |
| 5 | Black Pepper | Piper nigrum | 94-62-2 | Piperine | insecticide, fungicide | 0.71 | 0.14 | 0.019% | 0.019% |
| | Powdered Ancho Chili | Capsicum annuum | 404-86-4 | Capsaicin | pesticide, bud finisher | 0.71 | 0.14 | 0.019% | |
| 6 | Coriander | Coriandrum sativum | 8008-52-4 | Coriander Oil | insecticide, fungicide | 0.71 | 0.14 | 0.019% | 0.037% |
| | Salt | Sodium Chloride | 7647-14-5 | NaCl | Ionic catalyst | 0.34 | 0.07 | 0.009% | |
| | Cayenne | Capsicum annuum | 404-86-4 | Capsaicin | pesticide, bud finisher | 0.34 | 0.07 | 0.009% | |
| 7 | Cumin | Cuminum cyminum | 122-03-2 | Cuminaldehyde | insecticide, fungicide | 0.34 | 0.07 | 0.009% | 0.027% |
| 8 | Fenugreek | Trigonella foenum-graecum | 535-83-1 | Trigonelline | insecticide, fungicide | 0.17 | 0.03 | 0.004% | 0.004% |
| | Nutmeg | Myristica fragrans | 555-45-3 | Trimyristin | insecticide, fungicide | 0.09 | 0.02 | 0.002% | |
| 9 | Oregano | Origanum Vulgare | 499-75-2 | Carvacrol | insecticide, fungicide | 0.09 | 0.02 | 0.002% | 0.004% |
| | 1 gallon of water (3.79L) | Oxidane | 7732-18-5 | H2O | Dilution & spreading agent | 3785.41 | 767.99 | 98.65% | 98.65% |
| Total | | | | | | 3837.25 | 778.51 | 100.00% | 100.00% |

FIG. 14

MAGIC FLOWER - 3.1

| Tiers | Ingredients | Scientific Name | CAS# & Compound | Function | Teaspoons | Percentage | Tier Percentage |
|---|---|---|---|---|---|---|---|
| 1 | Garlic | Allium sativum | 539-86-6 Allicin | insecticide, fungicide | 0.5 | 4.76% | |
| | Ginger | Zingiber officinale | 122-48-5 Zingerone | fungicide | 0.5 | 4.76% | |
| | Cinnamon | Cinnamomum verum | 104-55-2 Cinnamaldehyde | insecticide, fungicide | 0.5 | 4.76% | 14.27% |
| 2 | Turmeric | Curcuma longa | 458-37-7 Curcumin | insecticide, fungicide | 0.25 | 2.38% | |
| | Clove | Syzygium aromaticum | 97-53-0 Eugenol | insecticide, fungicide | 0.25 | 2.38% | 4.76% |
| 3 | Black Pepper | Piper nigrum | 94-62-2 Piperine | insecticide, fungicide | 0.125 | 1.19% | 1.19% |
| 4 | Coriander | Coriandrum sativum | 8008-52-4 Coriander Oil | insecticide, fungicide | 0.09 | 0.86% | 0.86% |
| | Salt | Sodium Chloride | 7647-14-5 NaCl | | 0.06 | 0.57% | |
| | Powdered Ancho Ch | Capsicum annuum | 464-86-4 Capsaicin | pesticide, bud finisher | 0.06 | 0.57% | |
| | Cayenne | Capsicum annuum | 404-86-4 Capsaicin | pesticide, bud finisher | 0.06 | 0.57% | |
| 5 | Cumin | Cuminum cyminum | 122-03-2 Cuminaldehyde | insecticide, fungicide | 0.06 | 0.57% | 2.29% |
| 6 | Fenugreek | Trigonella foenum-graecum | 535-83-1 Trigonelline | insecticide, fungicide | 0.03 | 0.29% | 0.29% |
| | Nutmeg | Myristica fragrans | 555-45-3 Trimyristin | insecticide, fungicide | 0.015 | 0.14% | |
| 7 | Oregano | Origanum Vulgare | 499-75-2 Carvacrol | insecticide, fungicide | 0.015 | 0.14% | 0.29% |
| 8 | Sesame Oil | Sesamum indicum | 533-31-3 Sesamol | insecticide, fungicide | 3 | 28.53% | 28.53% |
| 9 | Apple Cider Vinegar | Malus sylvestris | 8028-52-2 Acetic acid | fungicide | 3 | 28.53% | 28.53% |
| 10 | Potassium Bicarbonate | potassium hydrogen carbonate | 298-14-6 chko3 | fungicide | 2 | 19.02% | 19.02% |
| Total | | | | | 10.515 | 100.00% | 100.00% |

FIG. 15

MAGIC FLOWER - 3.1

| Tiers | Ingredients | Scientific Name | CAS# & Compound | Function | Teaspoons | Percentage | Tier Percentage |
|---|---|---|---|---|---|---|---|
| 1 | Garlic | Allium sativum | 539-86-6 Allicin | insecticide, fungicide | 0.5 | 0.064% | 0.193% |
| | Ginger | Zingiber officinale | 122-48-5 Zingerone | fungicide | 0.5 | 0.064% | |
| | Cinnamon | Cinnamomum verum | 104-55-2 Cinnamaldehyde | insecticide, fungicide | 0.5 | 0.064% | |
| 2 | Turmeric | Curcuma longa | 458-37-7 Curcumin | insecticide, fungicide | 0.25 | 0.032% | 0.064% |
| | Clove | Syzygium aromaticum | 97-53-0 Eugenol | insecticide, fungicide | 0.25 | 0.032% | |
| 3 | Black Pepper | Piper nigrum | 94-62-2 Piperine | insecticide, fungicide | 0.125 | 0.016% | 0.016% |
| 4 | Coriander | Coriandrum sativum | 8008-52-4 Coriander Oil | insecticide, fungicide | 0.09 | 0.012% | 0.012% |
| | Salt | Sodium Chloride | 7647-14-5 NaCl | | 0.06 | 0.008% | |
| | Powdered Ancho Ch | Capsicum annuum | 404-86-4 Capsaicin | insecticide, fungicide | 0.06 | 0.008% | |
| | Cayenne | Capsicum annuum | 404-86-4 Capsaicin | insecticide, fungicide | 0.06 | 0.008% | |
| 5 | Cumin | Cuminum cyminum | 122-03-2 Cuminaldehyde | insecticide, fungicide | 0.06 | 0.008% | 0.031% |
| 6 | Fenugreek | Trigonella foenum-graecum | 535-83-1 Trigonelline | insecticide, fungicide | 0.03 | 0.004% | 0.004% |
| | Nutmeg | Myristica fragrans | 555-45-3 Trimyristin | insecticide, fungicide | 0.015 | 0.002% | |
| 7 | Oregano | Origanum Vulgare | 499-75-2 Carvacrol | insecticide, fungicide | 0.015 | 0.002% | 0.004% |
| 8 | Sesame Oil | Sesamum indicum | 533-31-3 Sesamol | insecticide, fungicide | 3 | 0.385% | 0.385% |
| 9 | Apple Cider Vinegar | Malus sylvestris | 8028-52-2 Acetic acid | fungicide | 3 | 0.385% | 0.385% |
| 10 | Potassium Bicarbonate | potassium hydrogen carbonate | 298-14-6 CHKO3 | fungicide | 2 | 0.257% | 0.257% |
| | 1 gallon of water | Oxidane | 7732-18-5 H2O | Dilution & spreading agent | 767.988 | 98.65% | 98.65% |
| Total | | | | | 778.503 | 100.00% | 100.00% |

FIG. 16

MAGIC FLOWER - 3.0

| Tiers | Ingredients | Scientific Name | CAS# & Compound | | Function | Teaspoons | Percentage | Tier Percentage |
|---|---|---|---|---|---|---|---|---|
| 1 | Garlic | Allium sativum | 539-86-6 | Allicin | insecticide, fungicide | 0.5 | 4.81% | |
| | Ginger | Zingiber officinale | 122-48-5 | Zingerone | fungicide | 0.5 | 4.81% | |
| | Cinnamon | Cinnamomum verum | 104-55-2 | Cinnamaldehyde | insecticide, fungicide | 0.5 | 4.81% | 14.43% |
| 2 | Turmeric | Curcuma longa | 458-37-7 | Curcumin | insecticide, fungicide | 0.25 | 2.41% | |
| | Clove | Syzygium aromaticum | 97-53-0 | Eugenol | insecticide, fungicide | 0.25 | 2.41% | 4.81% |
| 3 | Black Pepper | Piper nigrum | 94-62-2 | Piperine | insecticide, fungicide | 0.125 | 1.20% | 1.20% |
| 4 | Coriander | Coriandrum sativum | 8008-52-4 | Coriander Oil | insecticide, fungicide | 0.09 | 0.87% | 0.87% |
| 5 | Cayenne | Capsicum annuum | 404-86-4 | Capsaicin | insecticide, fungicide | 0.06 | 0.58% | |
| | Cumin | Cuminum cyminum | 122-03-2 | Cuminaldehyde | insecticide, fungicide | 0.06 | 0.58% | 1.15% |
| 6 | Fenugreek | Trigonella foenum-graecum | 535-83-1 | Trigonelline | insecticide, fungicide | 0.03 | 0.29% | 0.29% |
| 7 | Nutmeg | Myristica fragrans | 555-45-3 | Trimyristin | insecticide, fungicide | 0.015 | 0.14% | |
| | Oregano | Origanum Vulgare | 499-75-2 | Carvacrol | insecticide, fungicide | 0.015 | 0.14% | 0.29% |
| 8 | Sesame Oil | Sesamum indicum | 533-31-3 | Sesamol | insecticide, fungicide | 3 | 28.86% | 28.86% |
| 9 | Apple Cider Vinegar | Malus sylvestris | 8028-52-2 | Acetic acid | fungicide | 3 | 28.86% | 28.86% |
| 10 | Potassium Bicarbonate | potassium hydrogen carbonate | 298-14-6 | chko3 | fungicide | 2 | 19.24% | 19.24% |
| Total | | | | | | 10.395 | 100.00% | 100.00% |

FIG. 17

MAGIC FLOWER - 3.0

| Tiers | Ingredients | Scientific Name | CAS# & Compound | | Function | Teaspoons | Percentage | Tier Percentage |
|---|---|---|---|---|---|---|---|---|
| 1 | Garlic | Allium sativum | 539-86-6 | Allicin | insecticide, fungicide | 0.5 | 0.064% | |
| | Ginger | Zingiber officinale | 122-48-5 | Zingerone | fungicide | 0.5 | 0.064% | |
| | Cinnamon | Cinnamomum verum | 104-55-2 | Cinnamaldehyde | insecticide, fungicide | 0.5 | 0.064% | 0.193% |
| 2 | Turmeric | Curcuma longa | 458-37-7 | Curcumin | insecticide, fungicide | 0.25 | 0.032% | |
| | Clove | Syzygium aromaticum | 97-53-0 | Eugenol | insecticide, fungicide | 0.25 | 0.032% | 0.064% |
| 3 | Black Pepper | Piper nigrum | 94-62-2 | Piperine | insecticide, fungicide | 0.125 | 0.016% | 0.016% |
| 4 | Coriander | Coriandrum sativum | 8008-52-4 | Coriander Oil | insecticide, fungicide | 0.09 | 0.012% | 0.012% |
| 5 | Cayenne | Capsicum annuum | 404-86-4 | Capsaicin | insecticide, fungicide | 0.06 | 0.008% | |
| | Cumin | Cuminum cyminum | 122-03-2 | Cuminaldehyde | insecticide, fungicide | 0.06 | 0.008% | 0.015% |
| 6 | Fenugreek | Trigonella foenum-graecum | 535-83-1 | Trigonelline | insecticide, fungicide | 0.03 | 0.004% | 0.004% |
| 7 | Nutmeg | Myristica fragrans | 555-45-3 | Trimyristin | insecticide, fungicide | 0.015 | 0.002% | |
| | Oregano | Origanum Vulgare | 499-75-2 | Carvacrol | insecticide, fungicide | 0.015 | 0.002% | 0.004% |
| 8 | Sesame Oil | Sesamum indicum | 533-31-3 | Sesamol | insecticide, fungicide | 3 | 0.385% | 0.385% |
| 9 | Apple Cider Vinegar | Malus sylvestris | 8028-52-2 | Acetic acid | fungicide | 3 | 0.385% | 0.385% |
| 10 | Potassium Bicarbonate | potassium hydrogen carbonate | 298-14-6 | CHKO3 | fungicide | 2 | 0.257% | 0.257% |
| | 1 gallon of water | Oxidane | 7732-18-5 | H2O | Dilution & spreading agent | 767.988 | 98.66% | 98.66% |
| Total | | | | | | 778.383 | 100.00% | 100.00% |

FIG. 18

Magic Flower Formula (Version 1.0)

| Ingredient | Scientific Name | Quantity |
|---|---|---|
| Potassium bicarbonate | a/k/a potassium hydrogen carbonate or potassium acid carbonate | 2/3 Tbsp |
| Apple Cider Vinegar | Malus sylvestris | 1 Tbsp |
| Sesame Oil | Sesamum indicum | 1 Tbsp |
| Garlic Powder | Allium sativum | 4 parts |
| Ginger | Zingiber officinale | 4 parts |
| Cinnamon | Cinnamomum burmanii | 4 parts |
| Curry (corriander, tumeric, cumin, fenugreek, chili pepper) | | 2 parts |
| Turmeric | Curcuma longa | 2 parts |
| Cloves | Syzygium aromaticum | 2 parts |
| Black Pepper | Piper nigrum | 1 parts (small amount .01 oz of 128 oz) |
| Chile Powder | Capsicum annuum | 1 parts |

TRICHOME AND PISTIL MATURING FORMULATION

CROSS-REFERENCE TO RELATED APPLICATIONS

This patent application claims priority to U.S. Patent Application Ser. No. 62/285,987, entitled "Magic Flower" and filed on Nov. 16, 2015. This patent application claims priority to U.S. Patent Application Ser. No. 62/344,532, entitled "Trichome and Pistil Maturing Formulation", and filed on Jun. 2, 2016. The entire disclosures of these two provisional patent applications are hereby incorporated by reference.

STATEMENT REGARDING FEDERALLY SPONSORED RESEARCH OR DEVELOPMENT

Not applicable.

THE NAMES OF THE PARTIES TO A JOINT RESEARCH AGREEMENT

Not applicable.

INCORPORATION-BY-REFERENCE OF MATERIAL SUBMITTED ON A COMPACT DISC

Not applicable.

BACKGROUND OF THE INVENTION

1. Field of the Invention

This invention relates to food grade garden spray, and more particularly to such a natural formulation that is tasty to humans but also enhances scent, flavor, vigor and yield in plants by positively affecting vegetative reproductive anatomy and positively impacting beneficial insect relationships with plants while negatively impacting the environment for pests. The positive effects manipulated in the plants include control over expediting trichome maturation rates and pistil maturation rates, thus reducing flowering periods for plants having these structures.

2. Description of the Related Art

The commercial food industry is receiving increasing public pressure to provide natural products that have not been treated with synthesized chemicals. Harsh chemicals are no longer favored as pesticides or as fertilizers. Meanwhile, plant anatomy discoveries are allowing gardeners to provide crops of plants with the nutrients and conditions they need to succeed according to the gardener's goals. In both the gardening industry as well as in home gardens, gardeners are seeking to enhance vigor and yield for increased value. In addition to these goals, in the medicinal plant industry, enhancements are also being sought for the characteristics of potency and efficiency in maturation. Maximizing plant health and environmental conditions will naturally benefit the plant's immune system and ability to combat pest invasions, maladies or infections.

Growers of legal cannabis plants are under the same pressures as agriculturists tending other crops. Cannabis growers try to maximize yield and medical benefits of the harvested medical marijuana. In order to optimize plant growth, growers must learn the biology of the plants and how to best foster the natural plant processes. In this respect, cannabis plants have similarities to other crops and growers can rely on the wisdom of traditional horticulturalists. Techniques used on other crops where the plants have similar anatomy are particularly instructive and, likewise, techniques used to grow cannabis can be applied to other crops.

Important to, but not unique to, cannabis plants are trichomes and pistils. The pistils are the colored hairs that sprout on the flower part of cannabis (the 'bud'). Trichomes are single or multicellular outgrowths of the plant epidermis and collectively constitute the pubescence (hairiness) of the plant surface. Secretory and glandular trichomes (SGTs) populate the aerial surfaces of an estimated one-third of all vascular plant species. Scientific studies are just beginning to uncover all of the ways these unicellular and multicellular appendages function and they are proposed to play a critical role in plant protection against various biotic and abiotic stresses including herbivore attack, pathogen infection, extreme temperature, and excessive UV light. One of the most remarkable features of SGTs is their capacity to synthesize, store, and secrete large amounts of secondary metabolites. However, because they are not essential for plant survival, SGTs provide a unique opportunity to study complex and specialized metabolic pathways that operate within the confines of a simple and highly accessible developmental structure.

It is noteworthy that many trichome-borne compounds have significant commercial value as pharmaceuticals, fragrances, food additives, and natural pesticides. In fact, all of the psychoactive chemicals found to have benefits to humans are produced inside the trichome. The prospect of exploiting SGTs as "chemical factories" to produce high-value plant products has recently captured the attention of plant biochemists and biotechnologists alike. Medical marijuana growers are also learning that all of the chemicals which provide the medicinal qualities of the cannabis plant are found inside trichomes. Organelles produced by the plant called vacuoles contain phenols, a chemical compound similar to alcohol. Another type of organelle called plastids contain hydrocarbons called terpenes. Phenols and terpenes make their way up the trichome stalk and combine inside the secretory cavity to form a fibrous mat. This concentrated mat is hit by UV-B light waves, causing the creation of cannabinoids.

On the chemical level in the family Cannabaceae, Tetrahydrocannabinol (THC) and other cannabinoids are produced inside the heads of the trichomes. The trichomes of Cannabis sativa produce and accumulate the psychoactive tetrahydrocannabinol, which is synthesized through C10 prenylation of olivetolic acid, followed by a cyclization reaction and decarboxylation. The chemistry of the trichomes in the family Cannabaceae come into play in other industries as well. For example, in hops (*Humulus lupulus*), which provide flavor to beer, the trichomes contain, in addition to terpenes, many C5-prenylated polyketides, with the major compound being xanthohumol. Plants including *Echinacea*, Oxeye plants, Electric daisy, *helichrysum*, chocolate, black pepper, Peruvian maca, Chinese *rhododendron*, and liverwort may also have trichomes that create or house the pharmacological compounds found to interfere with pain receptors and therefore are useful in treating human ailments.

Besides housing the chemicals that benefit human health, trichomes also play a major role in the health of plants. Trichomes occur on at least a third of all plant species. Trichomes serve as taxonomical criteria and are known to be present on the surfaces of leaves, stems, fruits, and sepals and also on the margins of leaves and sepals. Previous reports have shown that there are glandular and nonglandular trichomes that function in plants to reduce heat load, increase tolerance to freezing, aid seed dispersal, enhance water absorption, protect plant structures from the harmful effects of UV-B, repel insects, and offer a means of protection against herbivores and pathogens. Trichomes may prevent water and snow from adhering to a plant's surface which could reduce fungal infections of the leaves and inhibit frost damage to plant cells. Trichomes provide a very small amount of shade to a plant and may possibly trap a thin layer of air next to the plant's surface which would also provide some control over the internal temperature. Essential oils (i.e. lavender, mint, etc.), which are also known to assist in the plant's natural repellent and attractant mechanisms, are created in trichomes. The impact of trichomes on plant scent is effectuated when they exude scents through nectar or other secretions found to play a part in pollinator attraction. Downward-pointing trichomes in the upright tube of the carnivorous pitcher plant (*Sarracenia*) create a "lobster pot" effect preventing the escape of prey. Beans (*Phaseolus*) have evolved fish-hook-shaped trichomes that help to anchor their climbing vines but the hooked feature is also defensive because leafhopper and aphid pests are impaled and captured by these hairs. Other crop plants in which glandular trichomes are being used to breed for pest resistance include strawberry (*Fragaria*), sunflower (*Helianthus*), and tobacco (*Nicotiana*). Trichomes of this type are common in the nightshade family (*Solanaceae*) and plant breeders have created new varieties of potatoes (*Solanum*) and tomatoes (*Lycopersicon*) that resist insect pests because of glandular hairs on their leaves and stems.

The traditional harvest window for most cannabis plant buds is known to open after at least forty percent (40%) of the white hairs of the pistils darkened and curled in. Optimum levels of THC will be accomplished if buds are harvested when fifty percent to seventy percent (50%-70%) of pistils have darkened. Optimum levels of cannabidiol (CBN) for the best calming effect will result if the buds are harvested when the pistils are showing seventy percent to ninety percent (70-90%) darkened pistils. With some strains, it is much harder to recognize when the time is right for harvest because their appearance differs. For example, some strains can keep most of their pistils white even when they are ready to be harvested. Pistils are sensitive and many things can age them, alter them, or turn them brown and cause withering, signaling a decayed, degraded product. Many plant treatment products can change the pistil color on the cannabis plant and are avoided for this reason. In its natural process, the plant pistils begin white, turn bright orange at their peak freshness, and then turn brown when they are overripe or decayed. Products have inadvertently accelerated the pistil color change in cannabis but they have consistently ruined the harvest because the trichomes do not automatically mature at the same rate as the pistils.

Because the trichomes are visible shiny crystals on the buds where the THC, CBD, and other medical compounds are stored, sophisticated grows of legal marijuana striving to maximize yield and medical benefits of the harvested product, will rely upon the status of the trichomes to dictate harvest windows. The trichomes, commonly referred to as the 'crystals' on the buds or sometimes called resin glands, appear as mushroom-looking growths on cannabis plants. They have a crystalline or frosty appearance and are seen accumulating on the bud leaves. They are also what makes cannabis so 'sticky'. When viewed through magnification, harvest time is evaluated by viewing the status of trichomes that have a little ball on top. Since these are what contribute the most to bud potency, being able to tell when they have reached their highest levels of THC helps growers choose the exact right time to harvest. If the cannabis or other plant has not finished maturing the trichomes, yet other aspects of the plant, like pistils, have fully matured, then the plant will need to be harvested before the plant's trichomes have matured proper medicine.

Cannabis typically flowers for eight to twelve (8-12) or more weeks before completing the flowering cycle. The two basic types of cannabis, Indica and Sativa are commonly mixed to create hybrid strains. Often harvest time drives the objectives in creating these hybrids. Predominantly Indica varieties take about eight (8) weeks to mature. Predominantly Sativa varieties take twelve to sixteen (12-16) weeks to mature, which is why the industry is heavily focused on Indica varieties. However, Sativa varieties are known for making people laugh and feel creative and social while providing very strong palliatives. Indica varieties are strong palliatives for body ailments but are known to wipe people out and make things dull. Thus, the two basic varieties have two, totally opposite effects. There is a commercial demand and medical need to mature trichomes in an expeditious and predictable manner in order to serve the industry with a full range of medicinal options.

As noted above, trichomes and glands are two defensive mechanisms plants have developed to defend against phytophagous insects. The mode of defense made possible by trichomes is determined by whether the trichomes are nonsecretory or glandular, as well as their density, length, shape, and degree of erectness. When present on the plant surface at high densities, nonsecretory trichomes create a physical barrier to insect feeding on the underlying surface or internal tissues. The hair-like trichomes act as physical barriers keeping smaller insects away from the leaf surface making walking along the stem or leaf of a plant difficult for insects, snails, and slugs, thereby offering some protective value to the plant. Trichome epidermal hairs in many plant species are specialized for defense against attack by insects and mites. Barrier defense is an important element of resistance to leafhoppers in cultivated crop plants such as alfalfa (*Medicago*), cotton (*Gossypium*), and soybean (*Glycine*).

The most elegant specializations of plant hairs for defense are glandular trichomes. Glandular trichomes secrete a variety of substances like oils which provide scent and flavor to some herbs, act as irritants, or digestive juices. Glandular trichomes and plant glands may exude a sticky substance that physically entraps and immobilizes insects or mites, or they may contain toxic constituents which spill into the surrounding tissue when the gland is ruptured, making it unpalatable or toxic. These toxins are generally weak and do not kill the insect directly, rather they retard insect growth and delay pupation. As a result, the insects are more vulnerable to disease, predation, and the environment. This careful balance which has evolved between plants and insects could be seriously disrupted if humans synthesize and introduce secondary plant toxin analogs as insecticides. Additionally, insects may develop a resistance to the analogs and thereby also develop a resistance to the natural toxin. Keeping the plant as healthy as possible will allow the plant to utilize its own, natural defenses.

When applied to plants, some spices are known to have a particular impact on insect life. Indian Black Pepper (*Piper Nigrum*) has appreciable amounts of piperine, which is an alkaloid and is irritating to the digestive tracts of most insects. Cumin (*Cuminum Cyminum*) suffocates and inhibits the various biosynthetic processes of insects. The cumaldehyde is an alkaloid which is a naturally occurring organic compound. Cinnamon (*Cinnamomum Verum*) contains the organic compounds cinnamaldehyde, cinnamyl acetate, anethole and eugenol. These naturally occurring compounds possess insect antifeedant properties in which the insect is discouraged from eating. Garlic (*Allium Sativum*) is rich in diallyl disulfide, which acts both as an insect repellant and is observed to have some limited toxic properties against the same. Turmeric (*Curcuma*) contains a polyphenol known as curcumin. Curcumin acts as a paralyzing agent to the insect and is also effective as a repellant. Fenugreek (*Trigonella Foenum Graecum*) often used as another name for curry, contains saponin, which has a highly toxic paralyzing effect on insects. Cloves (*Syzygium Aromaticum*) contain Eugenol which a member of the phenylpropanoids family. This organic compound is effective in attacking the central nervous system of the insect and this results in paralysis and death. Chili (*Capsicum*) is rich in capsaicin, which is in the amide family. Capsaicin causes irritation in the digestive tracts of insects and is primarily effective as a repellant. Ginger (*Zingiber Officinale*) has zingerone, shogaols and gingerols as its primary chemical compounds. Its primary purpose is as a repellent.

Prior inventions have used food-type substances as ingredients in pesticides, but have combined those products in such a way that they are no long recognized as edible. For example, Kaji (Jap. Patent #JPH08295601) uses casein as a primary ingredient. While technically consumable and used by some extreme body builders in casein shakes for the protein blast, studies have shown that casein causes diabetes and other diseases when eaten directly. A1 beta casein and its byproduct BCM7 have also been linked to cases of type I diabetes, digestive disorders, neurodegenerative disorders and heart disease. These issues have the most supportive evidence linking them to A1 beta casein but A1 beta casein may be associated with other health disorders as well. See http://www.naturalnews.com/033384_A1_beta_casein_milk.html. Meanwhile, Doty (U.S. Pat. No. 8,202,557) may or may not be edible, depending significantly on the amount used—the formulation of Doty calls for a dusting application—but 20% of the formulation is black pepper. The powdered product would have too much pepper to be palatable and potentially make it even inedible. Black pepper in such high ratios has the potential for stunting plant growth even if diluted into a liquid form.

Further to the prior art of Doty, it specifically discloses a powder for use by dusting upon plants as working against non-flying insects and says nothing about preventing repeat invasions. Doty uses black mustard which is known to be less effective and slows plant growth as would black pepper in the amount Doty uses. Both ingredients have a 'burn' factor for plants, except at really low levels, but Doty uses black pepper as the main ingredient in the recipe. Doty requires 10-14 days of recovery time and reapplication every week or two. Use of Doty on plants could result in permanent growth stunting. Doty also uses cilantro and has no vinegar or oil, leaving it less effective. Doty uses baking soda (bicarbonate of soda) but baking soda leaves a salt residue after the carbon dioxide reaction, which is harmful and slows plant growth. Doty asserts that new plant growth is observed within 10-14 days after use. The Doty spice combinations are widely variable, some even make up 5-20% of the product in variability. The Doty product has a reuse period of 21 days; more frequent use would burn plants. Doty takes 48-72 hours to begin working as disclosed. Doty lists its product as an irritant and instructs the user to wear protective gear because it will burn or cause a rash.

Other inventions have their own drawbacks. Wilson (U.S. Pat. No. 5,466,459) is wax based and will clog plant pores, harming its life cycles. Dezur (U.S. Pat. No. 5,614,203) contains silicates which dry out soil. Arimoto (U.S. Pat. No. 6,284,286 B1) contains sulfur which is harmful to bees and humans.

Trichome engineering is being developed to increase plant resistance. However, synthesizing the active elements of trichomes in order to increase plant resistance, runs the risk of creating super bugs and fungi that are resistant to normal plant defensive exudates. The better approach is that taken by the present invention to strengthen the plants by strengthening the trichomes with naturally occurring substances.

The spices people commonly consume and which are GRAS (generally recognized as safe) by the FDA and by the public over thousands of years of use have Latin names and chemical compound structures consumers generally do not recognize or understand. A comprehensive summary of the chemical structures associated with many spices can be found in the "Chemistry of Spices" resource edited by Villupanoor A. Parthasarathy and Bhageerathy Chempakam and T. John Zachariah, each from the Indian Institute of Spices Research, Calicut, Kerala, India and located online at http://catbull.com/alamut/Bibliothek/Chemistry_of_Spices.pdf which is incorporated as though fully set forth herein. Similar resources are readily available for all spice and kitchen compounds.

Cayenne pepper is know to stimulate the eye's tissues and to improve circulation in them. Herbs such as Rue (*Ruta Graveolens*) is used by some people to make the sight both sharp and clear, especially when the vision had become dim through over-exertion of the eyes. Elder flower in water can be used for treatment of the eye and for skin lotions. Golden Seal (*berberine*) can also be useful against bacteria and inflammation, as well in the eye to treat trachoma but generally Golden Seal can relieve inflamed eyes. Curcumin in turmeric is known as a treatment for the eyes for conditions such as glaucoma and conjunctivitis.

BRIEF SUMMARY OF THE INVENTION

The present invention is a precise formulation for the treatment of plants and particularly is a new and useful invention termed by the inventor as a "bud finisher" with a slight modification termed the "bud shield." While scientific studies work to fully understand the process of how trichomes operate or exactly which mechanisms control plant development, the present invention is a homemade remedy running neck and neck with science itself as it works to manipulate trichomes. The formula comprises a particular ratio of a specific set of spices and a combination of liquids all of which are edible and routinely consumed by humans in quantities similar to those claimed. The spices are food grade products manufactured for human consumption and comprise Garlic, Ginger, Cinnamon, Turmeric, Clove, Black Pepper, Powdered Ancho Chili, Coriander, Cayenne, Cumin, Fenugreek, Nutmeg, and Oregano. These spices in the particular ratio and measurements are mixed into a single combination with potassium bicarbonate in quantities relative to the other spices and ingredients. This formulation is empirically derived. Meanwhile, a liquid mixture is formed when sesame oil is mixed with apple cider vinegar also in a particular ratio to the whole. For use, the spice combination and the liquid mixture are added to water for ease of plant application. The resulting combination is applied to all surfaces of the plant such as by spraying. This food grade home and garden spray is a natural formulation that enhances scent, flavor, vigor and yield in plants by positively affecting vegetative reproductive anatomy and positively impacting beneficial insect relationships with plants while negatively impacting the environment for pests. The positive effects manipulated in a particular subset of plants include a controlled but expedited trichome maturation rate and a pistil maturation rate thereby reducing flowering periods for plants having these structures. When the bud finisher is used the trichome and pistil maturation rates are synchronized.

The preferred ingredient ratios are described by tiers, which are relative quantities between and among the other ingredients. At the ratios presented, the formula offers a unique synergy. The specific formulation for the "bud finisher" embodiment before it is added to water for application may be described as follows:

| Tier | Ingredients (Scientific Name) | mL | Ing. % | Tier % |
|---|---|---|---|---|
| 1 | Sesame Oil (*Sesamum indicum*) | 14.79 | 28.71% | |
| | Apple Cider Vinegar (*Malus sylvestris*) | 14.79 | 28.71% | 57.43% |
| 2 | Potassium Bicarbonate (KHCO$_3$) | 7.39 | 14.36% | 14.36% |
| 3 | Garlic (*Allium sativum*) | 2.84 | 5.52% | |
| | Ginger (*Zingiber officinale*) | 2.84 | 5.52% | |
| | Cinnamon (*Cinnamomum verum*) | 2.84 | 5.52% | 16.57% |
| 4 | Turmeric (*Curcuma longa*) | 1.42 | 2.76% | |
| | Clove (*Syzygium aromaticum*) | 1.42 | 2.76% | 5.52% |
| 5 | Black Pepper (*Piper nigrum*) | 0.71 | 1.38% | |
| | Powdered Ancho Chili (*Capsicum annuum*) | 0.71 | 1.38% | |
| | Coriander (*Coriandrum sativum*) | 0.71 | 1.38% | 4.14% |
| 6 | Cayenne (*Capsicum annuum*) | 0.34 | 0.66% | |
| | Cumin (*Cuminum cyminum*) | 0.34 | 0.66% | 1.33% |
| 7 | Fenugreek (*Trigonella foenum-graecum*) | 0.17 | 0.33% | 0.33% |
| 8 | Nutmeg (*Myristica fragrans*) | 0.09 | 0.17% | |
| | Oregano (*Origanum Vulgare*) | 0.09 | 0.17% | 0.33% |
| | TOTAL | 51.50 | 100.00% | 100.00% |

Meanwhile, the embodiment termed the "bud shield" excludes the vinegar and bicarbonate and thereby changes the relative percentages as specified herein. Salt, optionally included, can act as a preservative and catalyst but its presence is deleterious to plants even when minute amounts are applied. While the specific combination is unique and proprietary to the inventor, some combinations of ingredients may be replaced by pre-mixed spice mixes, particularly chilli chili powder and curry. Because the ingredients are commonly used in a kitchen, they are commonly measured in terms of the volume calculations of cups and spoons, particularly teaspoons ("tsp"). Also, because proportions are important, the ingredients may be referenced according to relative parts. These ingredients could vary widely, even up to 100%+ and still function to some degree as a pesticide or natural stimulus to negatively impact the pest or invader's environment. The original, bud finishing and bud shielding aspects of the formula have a more narrow range for functionality, as described herein except that the heat units associated with the ingredients may be allowed to vary from 5,000 heat units to the levels approaching or equal to 100,000 heat units covering a range from a weak to strong formulation.

This specific formula functions as a 'bud finisher', unlike a standard ripening agent, in that it ripens trichomes and pistils. The particular aspects of the present preferred formula actually control the pistil as well as the trichome maturation and bring them to peak maturation in a desirable synchronicity, as well as keep them in peak robust vigor longer. The bud shield matures trichomes but only slightly matures pistils. A grower can implement use of the bud finisher or the bud shield to exert a strong degree of control over the level of maturation. These aspects of the invention particularly pertain to the legal cannabis industry but can also be applied to any plants which have 'pistils' and 'trichomes' (mostly flowering plants). Unlike other products, the bud finisher turns pistil hair color in cannabis and also matures the trichomes at the same rate as the pistils. When treated with the bud shield, trichomes turn cloudy on plants as early as three (3) weeks into flowering instead of the six to eight (6-8) weeks typically expected. Amber trichomes can be achieved as early as seven (7) weeks into flowering when treated with bud shield, instead of the ten to twelve (10-12) weeks normally observed.

No product on the market attempts to do what these two Magic Flower embodiments accomplish and frankly most people don't even believe it is true until they observe it for themselves. The breadth and duration of the positive results seen after application of the present invention were unexpected. The present invention's ability to mature the trichomes in a controlled manner is a particularly unique and completely unexpected aspect of this invention. The present invention can reduce the typical flowering time for medical marijuana to as little as six (6) weeks instead of the normal, eight to sixteen (8-16) weeks. This saves around a month of operating costs, and also provides an entire extra harvest per year to the farmer. The present invention makes the Sativas style cannabis plants, having positive therapeutic benefits on mood and creativity, commercially competitive because it shortens the trichome maturation time and thus harvest time to as little as six (6) weeks as opposed to the normal twelve to sixteen (12-16) weeks. The bud shield is primarily for gardeners who want to mature trichomes while maturing pistils only a small degree. Currently, there is no product on the market which allows growers to choose how and when to mature trichomes and also pistils.

The primary agent which is maturing the trichomes is heat as supplied by the ingredients bearing heat units. If a chili powder variety used has too high of a heat content it will over-mature the pistils and push the trichomes to degrade prematurely. In the case of a cannabis plant it will turn the buds an undesirable, brown or amber color. The potassium bicarbonate is the agent maturing the pistils primarily and the heat units are the primary agent maturing the trichomes (as well as affecting the pistils). Thus, this invention is more broadly defined as comprising "*Capsicum annuum*", the genus which encompasses all hot peppers, rather than requiring chili powder. The quantity of the heat units in the formula will set the parameters of the preferred peppers meeting the objectives of the invention to provide the heat units required to create the trichome maturation effect.

A product which shows efficacy as a pesticide and is also a health tonic, bloom enhancer, pollinator attractant, and ripening agent like the present invention is completely new and nonobvious. The synergistic effect of all the ingredients of the present invention act together to positively impact all insect relationships with the plant. Since the present invention is maturing, strengthening and stabilizing trichomes then it is also strengthening the plant's own natural, immune defense capacity. By strengthening the plants own trichomes the present invention is giving it peak protective capacity without disturbing the natural balance in the interactions between plants and insects/pests. Healthy trichomes may have an impact on pollinator attraction, possibly more than the elements of the formula themselves. The fact that the formula is strengthening and stabilizing trichomes provides a profound effect on the plants, pests, and pollinators that interact with it. By strengthening the trichomes, which produce scent and attracts pollinators, it explains why the formula makes flowers bloom quicker and for longer with noticeably richer scent. Enhancing the trichomes necessarily enhances the pollinator attraction.

The present bud finisher formula has established efficacy as a pesticide when applied in a range of minimal and maximum amounts and with particular reapplication. The mechanisms by which each of the above ingredients impacts pests may include functionality as a digestive irritant, respiration inhibitor, cause of paralysis, or just a general deterrent or repellant. It is shown to target diseases/pests, including all invasive soft bodies insects, Japanese beetle, mites, thrips, whitefly, fleas, fungus gnats, scale, spider mites, aphids, etc., as well as powdery mildew, blackspot, downy mildew, blights, molds and other plant diseases. The bud shield formulation is less effective versus powdery mildew than the bud finisher and has little effect on Japanese beetles, however it is fully effective against mites and other soft bodied insects. For application purposes, either formulation of the present invention is diluted into 1 gallon of water. This combination is sprayed directly onto plants, leaves, stocks, soil, fruit, and flowers. This mixture in one gallon of water covers 100 square feet of dense foliage or 200 square feet of light to medium foliage. The application of this combination protects the plants for seven to fourteen (7-14) days in normal conditions or for as many as three or more days in heavily adverse conditions (such as existing infestation). The formula works against Japanese beetles which no other natural product currently does. The bud finisher's potassium carbonate provides a better coating effect on the plant interrupting the feeding ability of the Japanese beetle and others. While the bud finisher affects the nervous system of Japanese beetles, it does not harm and in fact attracts ladybugs, bees, hummingbirds, butterflies and other pollinators. Japanese beetles in a jar with a normal leaf will normally consume the leaf in two to twelve (2-12) hours and always within a twenty-four (24) hour period. When the leaf is sprayed with Bud Finisher the beetles move very slowly, often retracting their arms and it takes them two to three (2-3) days to finish eating the leaf. After exposure to the formula, the Japanese beetle mating activities are minimal. If the Bud Finisher treated leaf is removed and a fresh untreated leaf is replaced the beetles will revive and return to normal eating and mating. If an inch of Bud Finisher is left in the jar with a treated leaf, the beetles hardly move and some will lay upside down with their legs retracted, appearing dead, but will revive if they are removed from the jar. Japanese beetles avoid plants that have been sprayed for two to four (2-4) weeks after treatment. Ultimately, this product positively impacts trichome maturation and health which assists the plant in mounting its own defense against pests—quite different than pouring a poison on them that kills a pest, but then forces the plant to recover from the shock of the poison.

The present invention doubles as a food spice packet with recipes ranging from salad dressing, to table spice, to meat rub or rib soak, to chip dip and really any edible application. Applicant is seeking regulatory approval to have the present invention, Magic Flower, listed as a consumer food item and simultaneously as a pesticide, a novel idea and a uniquely difficult request. Once regulatory approval is in place, this formula will have a new and unique position in the pesticide industry. The regulatory challenges currently being encountered further substantiates that the regulatory process does not contemplate and is not equipped to deal with a product that is both a food product and a pesticide and this new product is unique and unforeseen to the industry or the regulatory agencies.

The present formulations are so safe that they can be sprayed in human eyes. When sprayed in the eyes, the Magic Flower bud finisher may stimulate circulation to the eyes. The application will feel only like water has been splashed into the user's eyes; however, immediate results of increased vision clarity are appreciable. Clearer vision and vibrant color perceptions are improved. Additionally, the effects of presbyopia are reduced. Users will be able to read easily at close range and see clearly at a close distance. The results continue after a single application for 2-3 days when re-application may be needed. Compared with the plant treatment formulations of the present invention, before the formula is applied to eyes it must go through additional filtration such as through a coffee filter or similar fine filter.

Because the formulation of the present invention contains spices which humans enjoy both to taste and smell, Magic Flower bud finisher is also desirable for use as incense, such as in an incense cone. When burning, it smells like a barbeque cooking and breathing the smoke is no more harmful than breathing the same spices while cooking on a barbecue. For Magic Flower to be sprayed on a product such as an incense stick that would later be burned to emit smoke would transmit a residue that would be far less than that typically inhaled while cooking in front of a barbecue grill.

The foregoing has outlined, in general, the physical aspects of the invention and is to serve as an aid to better understanding the more complete detailed description which is to follow. In reference to such, there is to be a clear understanding that the present invention is not limited to the method or detail of construction, fabrication, material, or application of use described and illustrated herein. Any other obvious variation of fabrication, use, or application should be considered apparent as an alternative embodiment of the present invention.

BRIEF DESCRIPTION OF THE DRAWINGS

The following drawings further describe by illustration, the advantages and objects of the present invention. Each drawing is referenced by corresponding figure reference characters within the "DETAILED DESCRIPTION OF THE INVENTION" section to follow.

FIG. 8 is a table showing the ingredients of the bud finisher formula of the present invention before they are mixed with water.

FIG. 9 shows the resulting ratios of all ingredients when the bud finisher formula shown in FIG. 8 is added to a gallon of water.

FIG. 10 is a table showing the ingredients of the bud shield formula of the present invention before they are mixed with water.

FIG. 11 shows the resulting ratios of all ingredients when the bud shield formula shown in FIG. 10 is added to a gallon of water.

FIG. 12 is a table showing the ingredients of the 3.2 Magic Flower formula of the present invention before they are mixed with water.

FIG. 13 shows the resulting ratios of all ingredients when the 3.2 Magic Flower formula shown in FIG. 12 is added to a gallon of water.

FIG. 14 is a table showing the ingredients of the 3.1 Magic Flower formula of the present invention before they are mixed with water.

FIG. 15 shows the resulting ratios of all ingredients when the 3.1 Magic Flower formula shown in FIG. 14 is added to a gallon of water.

FIG. 16 is a table showing the ingredients of the 3.0 Magic Flower formula of the present invention before they are mixed with water.

FIG. 17 shows the resulting ratios of all ingredients when the 3.0 Magic Flower formula shown in FIG. 16 is added to a gallon of water.

FIG. 18 is a table showing the ingredients of an early alternative embodiment Magic Flower 1.0 formula of the present invention before they are mixed with water.

DETAILED DESCRIPTION OF THE INVENTION

The 'bud finisher' and 'bud shield' aspects of the present invention are revolutionary. However, the formula iterations (mostly flowering plants). The present invention is the only one of its kind that turns pistil hair color in cannabis while it prevents the ruining of the harvest as is seen when the 'trichomes' do not automatically mature at the same rate as the pistils. The originality of the bud finisher embodiment lies in its ability to trigger the plant to mature the trichomes in synchronicity with the pistils. The treated plants grow more vigorously, producing a greater number of flowers and fruits or vegetables. The present invention was years in development. There is no product on the market which does this and the results are unexpected.

This product has profound effects on cannabis plants maturing the trichomes for medicinal marijuana and causing them to ripen and become ready 25-50% more quickly. This has big implications for that industry.

The 'bud finisher' and 'bud shield' aspects of the present invention are truly the most unusual and unforeseeable aspect. This is not a standard ripening agent, the formulas specifically ripen trichomes and pistils with a strong degree of control over the level of maturation. This aspect is unique to this product and it is this primary function the inventor seeks to protect. Currently there is no product on the market which matures trichomes.

Figure 1:
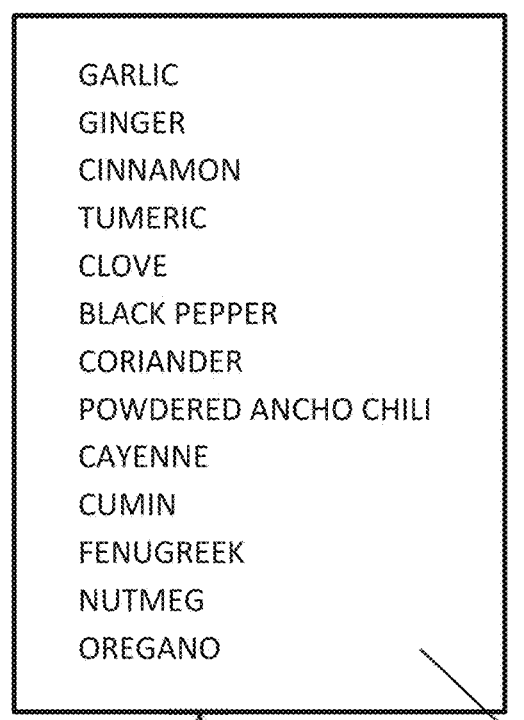
FIG. 1 is a schematic diagram of the powdered spice ingredients which are filtered and combined with potassium bicarbonate in a first container, Jar A.
Figure 1:
Figure 1:
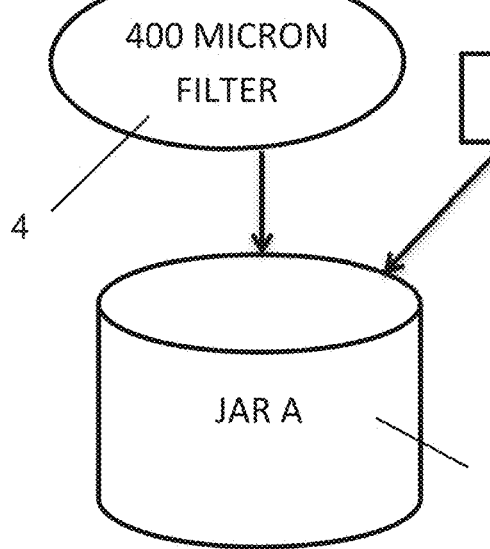
Figure 2:
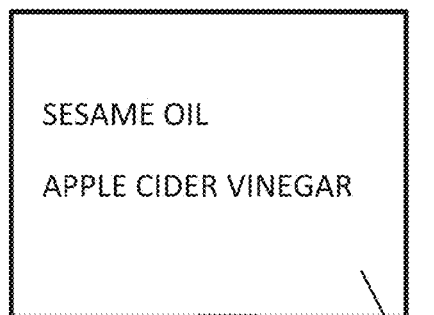
FIG. 2 is a schematic diagram demonstrating the liquid ingredients of sesame oil and apple cider vinegar being combined into a second container, Jar B.
Figure 2:
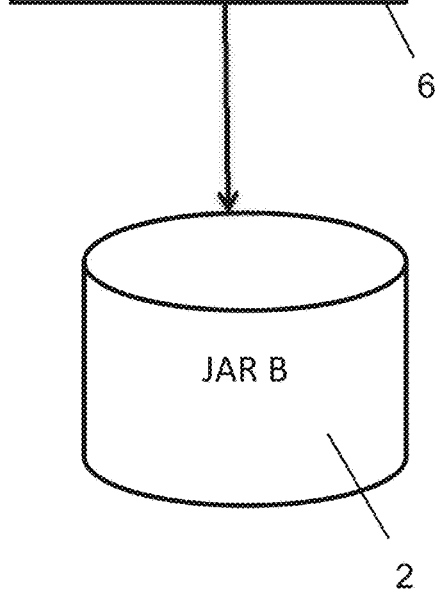
Figure 3:
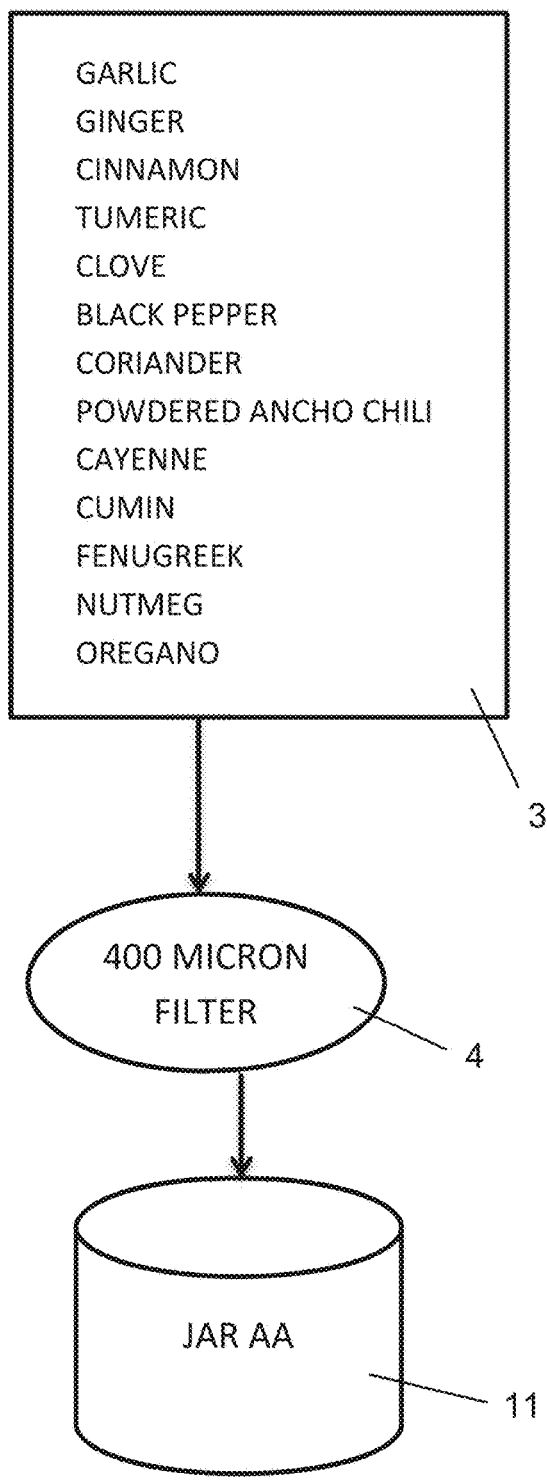
FIG. 3 is a schematic diagram of the powdered spice ingredients which are filtered and combined with potassium bicarbonate in a first container, Jar AA.
Figure 4:
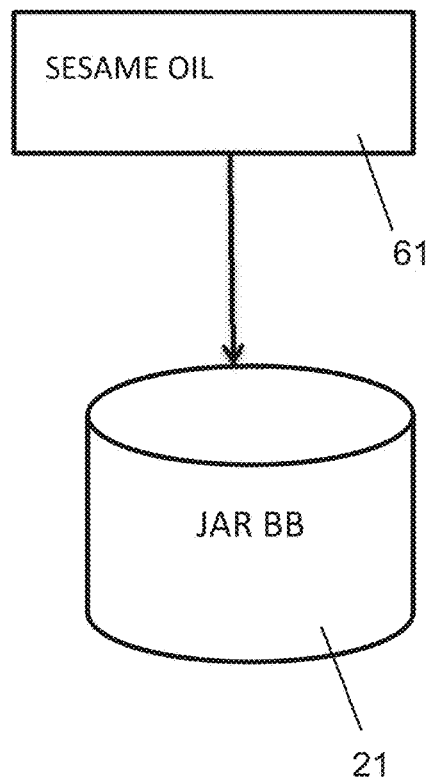
FIG. 4 is a schematic diagram demonstrating the liquid ingredients of sesame oil being inserted into a second container, Jar BB.

The embodiments of the present invention, sold to consumers under the commercial name of Magic Flower sprays, may be packaged in kits or as premixed spray treatments. When it is shipped to the consumer as a kit, the bud finisher embodiment of the present invention is represented in FIGS. 1-2. The shipment containers represented as Jar A 1 and Jar B 2 are packaged separately but are jointly sold together. The kit product is accompanied by instructions for combining the mixtures with water prior to application. As illustrated in FIG. 1, the first box represents the spices 3 which are also identified as the dry ingredients listed with their chemical name, CAS, %, and known function, comprising the following:

| | | | |
|---|---|---|---|
| Garlic (*Allium sativum*) | 539-86-6 | Allicin | insecticide, fungicide |
| Ginger (*Zingiber officinale*) | 122-48-5 | Zingerone | fungicide |
| Cinnamon (*Cinnamomum verum*) | 104-55-2 | Cinnamaldehyde | insecticide, fungicide |
| Turmeric (*Curcuma longa*) | 458-37-7 | Curcumin | insecticide, fungicide |
| Clove (*Syzygium aromaticum*) | 97-53-0 | Eugenol | insecticide, fungicide |
| Black Pepper (*Piper nigrum*) | 94-62-2 | Piperine | insecticide, fungicide |
| Coriander (*Coriandrum sativum*) | 8008-52-4 | Coriander Oil | insecticide, fungicide, pollinator attractant |
| Powdered Ancho Chili (*Capsicum annuum*) | 404-86-4 | Capsaicin | pesticide, trichome maturation |
| Cayenne (*Capsicum annuum*) | 404-86-4 | Capsaicin | pesticide, trichome maturation |
| Cumin (*Cuminum cyminum*) | 122-03-2 | Cuminaldehyde | insecticide, fungicide |
| Fenugreek (*Trigonella foenum-graecum*) | 535-83-1 | Trigonelline | insecticide, fungicide |
| Nutmeg (*Myristica fragrans*) | 555-45-3 | Trimyristin | insecticide, fungicide |
| Oregano (*Origanum Vulgare*) | 499-75-2 | Carvacrol | insecticide, fungicide. | of the present invention have established efficacy in a radical range of applications which are unexpected and go against conventional wisdom. Some of these incongruous applications discussed herein include an insecticide which also works to flavor food for human consumption, a fungicide which smells so nice it is used as an incense cone, and a pollinator attractant which also serves as a therapeutic eye wash. While the formula has unique industry and commercial applications to the legal cannabis industry, its application will benefit the health, blooms and ripening of any plants and particularly those having 'pistils' and 'trichomes'

In the kit embodiment, the second box shown in FIG. 1 indicates the addition of the following, unfiltered ingredient 5:

| | | | |
|---|---|---|---|
| Potassium Bicarbonate (KHCO$_3$) | 298-14-6 | khco3 | fungicide, pistil maturation. |

Salt, optionally included, can act as a preservative and catalyst but its presence is deleterious to plants even when minute amounts are applied. This is also why baking soda is less desirable than potassium bicarbonate. Soda leaves sodium behind which is deleterious to plants whereas potassium is generally beneficial.

As also demonstrated in FIG. 1, these dry ingredients are passed through a 400 Micron filter 4 and placed into Jar A 1. Meanwhile, the following wet ingredients 6 are also added to Jar B in FIG. 2:

| Sesame Oil (*Sesamum indicum*) | 533-31-3 | Sesamol | insecticide, fungicide, spreading agent |
| Apple Cider Vinegar (*Malus sylvestris*) | 8028-52-2 | Acetic acid | fungicide. |

Figure 6:
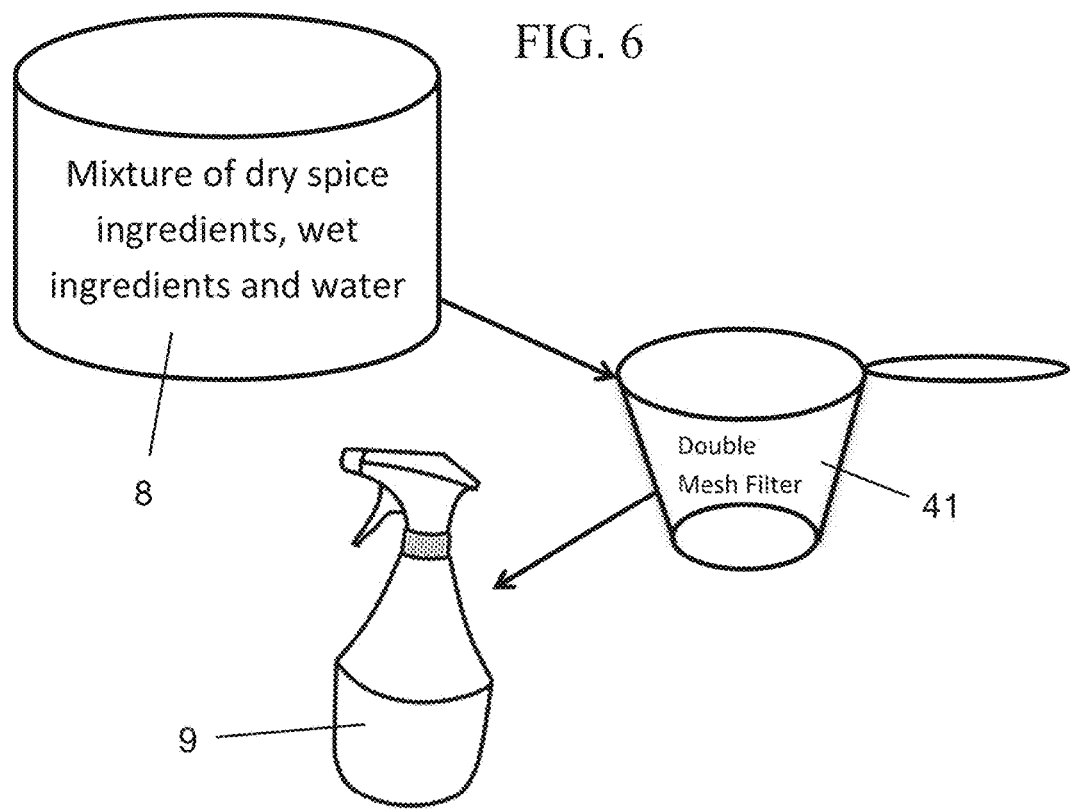
FIG. 6 is a schematic representation illustrating that the combined dry, liquid, and water mixture is transferred into a spray bottle prior to application.

Magic Flower bud finisher is passed through a double mesh filter before being added to the sprayer. A similar filter could be used, but the double mesh or 400 Micro Filter is known to remove possible spice debris that could cause clogging of a spray bottle during later use. As referenced in FIG. 6 additional double mesh filtering 41 is used to further prevent clogging. If clogging remains a problem then additional filtering should be implemented.

The complete bud finisher formulation with claimed ratios (indicated by "tiers") and quantities (indicated by milliliters ("mL")) before being added to water is illustrated in FIG. 8. Then, FIG. 9 illustrates the formula as diluted in water. The tiers are indicators of relative ratios. Each tier is tabulated for the tier totals and the ingredients are listed by common name as shipped to the consumer as follows:

| Tier | Ingredients (Scientific Name) | mL | Ing. % | Tier % |
|---|---|---|---|---|
| 1 | Sesame Oil (*Sesamum indicum*) | 14.79 | 28.71% | \| |
| | Apple Cider Vinegar (*Malus sylvestris*) | 14.79 | 28.71% | 57.43% |
| 2 | Potassium Bicarbonate ($KHCO_3$) | 7.39 | 14.36% | 14.36% |
| 3 | Garlic (*Allium sativum*) | 2.84 | 5.52% | \| |
| | Ginger (*Zingiber officinale*) | 2.84 | 5.52% | \| |
| | Cinnamon (*Cinnamomum verum*) | 2.84 | 5.52% | 16.57% |
| 4 | Turmeric (*Curcuma longa*) | 1.42 | 2.76% | \| |
| | Clove (*Syzygium aromaticum*) | 1.42 | 2.76% | 5.52% |
| 5 | Black Pepper (*Piper nigrum*) | 0.71 | 1.38% | \| |
| | Powdered Ancho Chili (*Capsicum annuum*) | 0.71 | 1.38% | \| |
| | Coriander (*Coriandrum sativum*) | 0.71 | 1.38% | 4.14% |
| 6 | Cayenne (*Capsicum annuum*) | 0.34 | 0.66% | \| |
| | Cumin (*Cuminum cyminum*) | 0.34 | 0.66% | 1.33% |
| 7 | Fenugreek (*Trigonella foenum-graecum*) | 0.17 | 0.33% | 0.33% |
| 8 | Nutmeg (*Myristica fragrans*) | 0.09 | 0.17% | \| |
| | Oregano (*Origanum Vulgare*) | 0.09 | 0.17% | 0.33% |
| | TOTAL | 51.50 | 100.00% | 100.00%. |

The bud shield embodiment of the present invention may also be packaged in kits or as premixed spray treatments. When it is shipped to the consumer as a kit, the bud shield embodiment of the present invention is represented in FIGS. 3-4. Jar AA 11 and Jar BB 21 are packaged separately but joined and sold together. The kit product is again accompanied by instructions for combining the mixtures with water prior to application. As illustrated in FIG. 3, the first box represents the spices 3 which are identical to the bud finisher spice mixture. There is no addition of potassium bicarbonate to the bud shield Jar AA, but the spices are filtered through a 400 micron filter to help prevent clogging once the mixture is added to liquids.

Meanwhile, for the bud shield only sesame oil serves as the wet ingredient 6 in Jar BB of FIG. 4:

| | | | |
|---|---|---|---|
| Sesame Oil (*Sesamum indicum*) | 533-31-3 | Sesamol | insecticide, fungicide, spreading agent. |

The complete bud shield formulation with claimed ratios (indicated by 'tiers') and quantities (indicated by milliliters) before being added to water is illustrated in FIG. 10. The tiers are indicators of relative ratios. Each tier is tabulated for the tier totals and the ingredients are listed by common name as shipped to the consumer as follows:

| Tier | Ingredients (Scientific Name) | mL | Ing. % | Tier % |
|---|---|---|---|---|
| 1 | Sesame Oil (*Sesamum indicum*) | 14.79 | 50.44% | 50.44% |
| 2 | Garlic (*Allium sativum*) | 2.84 | 9.70% | \| |
| | Ginger (*Zingiber officinale*) | 2.84 | 9.70% | \| |
| | Cinnamon (*Cinnamomum verum*) | 2.84 | 9.70% | 29.10% |
| 3 | Turmeric (*Curcuma longa*) | 1.42 | 4.85% | \| |
| | Clove (*Syzygium aromaticum*) | 1.42 | 4.85% | 9.70% |
| 4 | Black Pepper (*Piper nigrum*) | 0.71 | 2.42% | \| |
| | Powdered Ancho Chili (*Capsicum annuum*) | 0.71 | 2.42% | \| |
| | Coriander (*Coriandrum sativum*) | 0.71 | 2.42% | 7.27% |
| 5 | Cayenne (*Capsicum annuum*) | 0.34 | 1.16% | \| |
| | Cumin (*Cuminum cyminum*) | 0.34 | 1.16% | 2.33% |
| 6 | Fenugreek (*Trigonella foenum-graecum*) | 0.17 | 0.58% | 0.58% |
| 7 | Nutmeg (*Myristica fragrans*) | 0.09 | 0.29% | \| |
| | Oregano (*Origanum Vulgare*) | 0.09 | 0.29% | 0.58% |
| | TOTAL | 29.32 | 100.00% | 100.00%. |

For application, whether it is the Jar A 1 and Jar B 2 of the bud finisher or the Jar AA 11 and Jar BB 21 of the bud shield, they are combined as shown in FIG. 5 into a container of water 7. This combination can occur in any order and while less desirable and not illustrated, Jar A 1 could be combined with Jar B 2 in a container big enough to contain the carbon dioxide reaction and then added to the water. Though no carbon dioxide reaction would occur, the bud shield ingredients of Jar AA 11 and Jar BB 21 could be mixed together before being mixed into the water 7.

Growers apply the bud finisher to protect plants from adversity of all types because the treatments protect plants by strengthening the trichomes. The application of the present invention will protect the plant from unexpected weather variations. Under normal circumstances when a cannabis plant is exposed to daily temperatures peaking around 96 degrees, the product usually sours and turns to hay from the heat stress. With Magic Flower sprays actively applied over a two month period of these conditions, while the heat stress did cause yields to be cut in half, the product that did come out was still fresh with robust smell indicating intact terpenes and other trichome compounds. By strengthening the trichomes, Magic Flower sprays enable plants to greatly bolster their own natural defense system against temperature extremes.

The bud finisher embodiment slows down the pistil maturation as well as enhancing the trichome maturation. The bud shield enables trichomes to mature while not impacting pistils. The complete formulation has a series of alternative embodiments all of which have equal efficacy against insect infestations and some of which are shown in FIGS. 12-18.

FIG. 12 and FIG. 13 illustrates the Magic Flower formula 3.2 before and after it is mixed with water. The 3.2 Magic Flower mixture still included salt. Other formulations include the following:

Formula 1—original formula (see FIG. 18);
Formula 2—curry reformulated recipe analyzed and core ingredients replicated singly;
Formula 3—chili powder reformulated (see FIGS. 16 and 17);
Formula 3.1—powdered ancho chilis and salt added (see FIGS. 14 and 15); and
Formula 3.2—chili increase and potassium bicarbonate (KHCO$_3$) decreased (see FIGS. 12 and 13).

The alternative formulas may serve as a more ideal pesticide, such as Formula 1 or Formula 2. The later formulas were arrived at after much experimentation and trial and error. Ingredients were removed, reintroduced, reduced, increased and each time the tests for efficacy, optimization and performance were repeated. In the various alternative embodiments particular ingredients may move between tiers so that their percentages are changed relative to the other ingredients in order to make a change in efficacy. Iterations of the formula have evolved in part because while some ingredients were thought to be disadvantageous to plants, the removal and reintroduction have showed otherwise. In particular, cayenne pepper is beneficial to trichome maturation. The benefits of the preferred embodiment of the present invention are enhanced when powdered ancho chili is added to the formula. Adding ancho to the formula creates a synergy with the cayenne and speeds up trichome maturation by increasing the heat units. This collaboration brings the trichome maturation in closer step with the maturation of the pistils and thus encourages them to finish properly at the same time for maximum harvest speed, yield and product quality. Particular items in the complete formulation or in the alternative formulations may have the ability to be substituted with oils rather than the powdered version of the spice compound. For example, oregano may be substituted with oregano oil. In these case, the mixing of jar contents or containers may be altered slightly to accommodate the alternative state of matter.

The preferred formulas increase the amount of ancho chili powder to speed trichome maturation, and decreases potassium bicarbonate (also known as Potassium Hydrogen Carbonate—KHCO$_3$) to slow down pistil maturation so that the trichomes may mature at a similar rate. The tiers list ingredients in descending order of quantity in the recipe. While milliliters are shown for metric comparison, the preferred measurements are made in units of parts, spoons and/or cups as available in a typical kitchen.

The formulas without the cayenne still acts as a 'bud finisher' but at a much slower rate. The cayenne kicks it into high gear and the amount of cayenne can be varied, with more cayenne speeding up trichome maturation at a faster rate. Also, other hot peppers can be substituted for cayenne, such as powdered chilies, as long as it provides 30,000 to 50,000 heat units in approximately ¼th tsp-1/16th tsp per gallon of water. The 30,000 to 50,000 heat units at ⅛th tsp per gallon of water is ideal, but any food substance can be used if it provides as wide a range as 5,000 to 100,000 heat units. The higher the heat units, the quicker the trichome maturation acceleration. The ideal range is ¼ tsp-1/16 tsp per gallon of water. The ingredients for this aspect of the invention formula would still have similar effects if they were reduced by as much as 75% or increased to 200%+ and would have a corresponding reflection in maturation rates directly relative to their quantity.

Relative to the pesticide action, the formula could work to repel insects and molds with just the two active ingredients of sesame oil and potassium bicarbonate. Trials were done with sesame oil alone, in place of bud finisher and bud shield embodiments. The sesame oil is the primary active ingredient for deterring insects but did little against powdery mildew. Sesame oil had little effect on pistils or trichomes. Potassium bicarbonate is very effective against mold and mildew but has little to no effect on trichomes, yet fully matures pistils quickly in even small amounts. Vinegar alone did little for mites but was moderately effective against powdery mildew. It had little effect on pistils or trichomes. The spice packet may be referred to as a 'propellant' for the formula; however, it increases the pesticide features and is also key to maturing the trichomes. The Magic Flower Bud Finisher and Bud Shield spice packet is what primarily matures the trichomes, and that is the central and essential new use.

By way of example and not limitation, the following ingredients of the present invention combine in a synergistic manner to comprise a more effective insecticide than any one of the individual components. *Piper Nigrum, Cuminum Cyminum* and *Brassica Nigra* work together to attack the respiratory systems of insects by significantly increasing the rate of carbon dioxide production and thus induce suffocation. *Cinnamomum Verum, Foeniculum Vulgare* and *Capsicum* attack the insect's digestive ability by its action as an ion channel-type receptor. *Allium Sativum, Coriandrum Sativum* and *Capsicum* operate in concert to repel insect activity mainly due to the presence of diallyl trisulfide which has a repulsive effect upon many insect species. *Coriandrum Sativum, Curcuma, Trigonella Foenum Graecum* and *Syzygium Aromaticum* cause paralysis in the insect through the presence of linalool. *Murraya koenigii* (Curry tree) acts to inhibit the feeding activity of insects and doubles as a growth inhibitor this is primarily due to the presence of triterpenoid compounds which metabolize to indole alkaloids in the insect. The botanical constituents all work in synergism as a most effective bio-pesticide through several paths; repelling, inhibiting digestion, inducing paralysis and suffocating. Ingestion, repellency and digestive disruption are the initial frontline defenses and those insect species which are immune to these defenses then face paralysis as the secondary line of defense and finally those species which are not fully deterred by the above face certain extinction with the final and most formidable line of defense: suffocation. In an infestation where the plants were in full flower, one of them had so many spider mites that they had begun to form webs on the plant. Usually, infestations reaching the webbing point result in total loss of the crop. The plants that had been sprayed for powdery mildew were in perfect condition without one dot of mite damage. Spraying Bud Finisher that day completely controlled and suppressed the mite invasion. The crop thrived and the plants had leaves reaching up to the light while under full attack from mites but the plants were able to seal the mites out finish normally. The product was usable. Later, no spider mites have survived quarantine after one week either Magic Flower spray. When using Magic Flower sprays, no other sprays for pests are necessary.

The ingredients of the formulas are generally recognized as safe (GRAS) by the FDA and usually found in everyone's kitchen should be considered non-toxic in general, particularly in the minor amounts used in the formulas, based on the fact that no warnings are issued for their use anywhere in society. Among the present inventions uses are: pesticide, insecticide, fungicide, mosquito, flea and tick repellant, bud finisher, pollinator attractant, potassium fertilizer, immune booster, Japanese beetle spray, scent enhancer, pollinator attractant, blossom multiplier, carbon dioxide supplement, ripening agent, leaf polish (vegan), a plant wash or conditioner, an edible food (edible and palatable for human consumption), an eye wash or an incense cone. The invention can be used on all food crops, ornamentals, trees, bushes, shrubs, and flowers. It can be applied to all stages of growth from seedling, through harvest and curing. For the embodiment where mixing of two combinations together with water is done by the customer at the point of use to create extra carbon dioxide is new. Spices applied according to the present invention are even beneficial to human health if consumed on a sprayed product, so any residue would be beneficial. The present formula removes molds or soft bodied insects as well as Japanese beetles and forms a protective barrier against their return for seven to fourteen (7-14) days.

The aspects of the bud finisher embodiments of present invention have been found to:
1. eradicate mold, fungi or mildew and prevents their return for at seven to fourteen (7-14) or more days;
2. completely control spider mites, aphids, scale, thrips, whitefly and other soft bodied insects and prevents their return for seven to fourteen (7-14) or more days;
3. create a hostile environment for Japanese beetles and repels their return for seven to fourteen (7-14) or more days;
4. generate carbon dioxide while forming a byproduct of potassium which assists in plant health. Carbon dioxide increases weight, density and potency;
5. seal flowers and fruit, quicken ripening, hold flowers ripe longer with increased and stabilized scent;
6. mature resin glands and trichomes (particularly important to medical cannabis production);
7. attract pollinators by being harmless and attractive to ladybugs, bees, hummingbirds, dragonflies, and other diverse pollinator species;
8. increase flowering sites and number of blooms as well as hardiness.
9. bring older, unproductive plants back to full productivity, extend harvests length and quantity;
10. improve plant immunities and vigor, helping them replenish the beneficial microbes (microflora) in their individual micro-ecosystem;
11. be edible and in fact tasty, include spices known to benefit human health, also add potassium to the diet.

The bud shield also maintains these efficacies, but exerts less control over Japanese beetle populations.

One challenge with insecticides and fungicides is that they wipe out beneficial bacteria in the plant's microecosystem. The present invention employs an immune boosting formula that enhances plant vigor so it can replenish its useful biology, giving it further resistance to reinfection. Users of the formula can expect to go longer and longer between treatments as the plant regenerates its natural ability for self-protection.

The present invention is non-obvious because it is:
1. using spices in powder form which is something unconventional and illogical in an industry where oils are the standard;
2. a completely unique mix and no other combination of products could be used to arrive at this product and its effects. There is no antecedent or precursor to this formula;
3. incorporating spices put through a silk screen filtering process, so they are different than they would be if found in nature or from a store shelf;
4. a completely unique mixture of spices which are not currently used in any other pesticide product, nor found in this combination or with the suggestion of this combination in any commercial spice packet;
5. the synergy of the spices in exact proportion which creates the effect, this spice combination and proportion would be unprecedented from the pesticides before it and would not be discovered in a logical way.

The original packaging is a good idea for starting through internet/mail order to reduce shipping costs, however eventually the public will desire a bottled version already in suspension. Vacuum sealed, this formula will survive shelf storage for an acceptable amount of time in months or years and can be date stamped with a "best used by" date. For Internet/mail order shipping, the dry ingredients listed in Tiers 2 through 8 are combined into a single container, while the liquid ingredients listed in Tier 1 are combined into a second container. The end consumer purchases both as a set and mixes the ingredients of the two containers into another container of water, and then applies, such as by spraying the resulting mixture directly onto a plant including stem, foliage, yield and surrounding soil. The spray can be used at any stage of plant growth from seedling through harvest and curing. The current formulation distributed in jars will move into a vacuum sealed package also.

The bud finisher product sold to consumers in the kit packaging include the following instructions:

To Use

Figure 7:
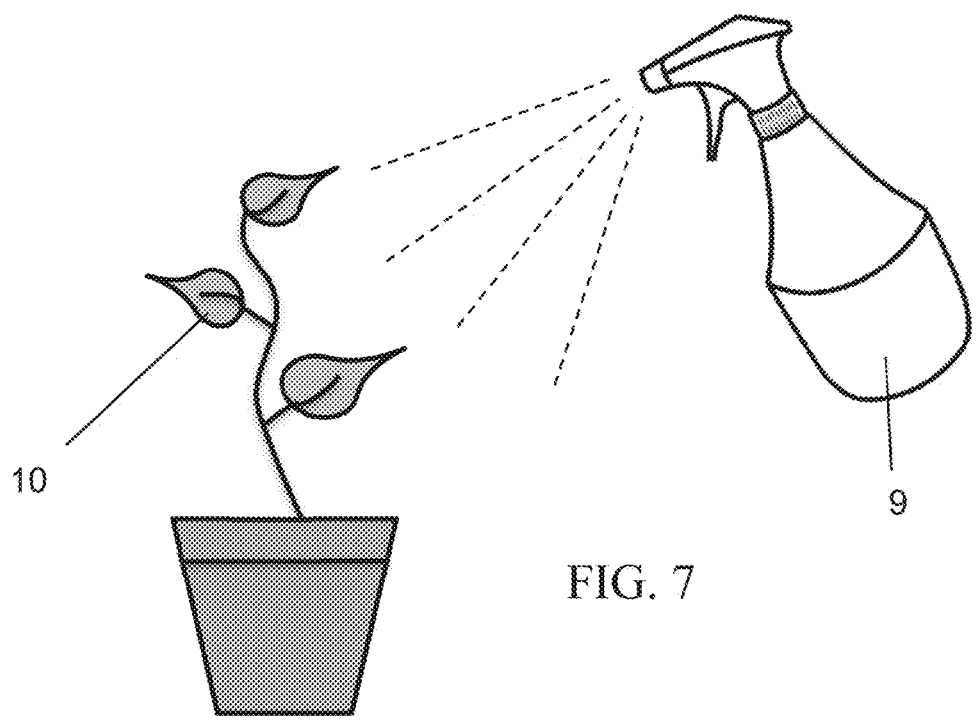
FIG. 7 schematically depicts how the combination created substantially as illustrated in FIGS. 1-6 is applied to a plant.

Add all ingredients to a gallon of water 7. Shake or mix well. Pour the final mixture 8 through a double mesh screen 41, into a convenient applicator such as a spray bottle 9 shown in FIG. 6. Apply directly to plants 10 over and under the leaves and flowers and upon the soil. Plant foliage should be sprayed on all surfaces until the solution is dripping off. Spray every 1-7 days as preferred as illustrated in FIG. 7. Refrigerate unused portion. One gallon covers 100-200 square feet.

For Salad Dressing and Marinade Mix

Mix together 1 cup olive oil, ½ cup vinegar and add Magic Flower to taste, let fizz settle. Makes 6-24 cups of dressing per commercial package of the spice pack.

The bud shield is primarily a product designed to be used by medical cannabis growers between weeks three (3) and six (6) of the flowering cycle so that the plants can mature trichomes but leave their pistils intact and not over matured. Some people prefer the amber trichomes which occur when the cloudy THC crystal ages to the point of decay and breaks down into CBN. CBN benefits are different than those in THC. The bud shield is the master formula which can be used on any crops for their entire life cycle, from seedling to finish.

The bud finisher is an effective personal mosquito repellant. Mosquitos may hover but will not land in areas sprayed. It is more effective than the other natural brands tested, all of the other natural formulas allow mosquitoes to bite. With the use of bud finisher not one bite was detected. It is also effective against ticks. In one test, when traveling through a tick infested area, the researcher attracted four ticks within ten (10) minutes before spraying. After spraying with diluted Bud Finisher and repeating the procedure, not one tick was observed. Spraying in a ten foot circle prevented all ticks, mosquitoes, and horse flies from entering a designated area. The primary drawback with its use as a personal insect repellent is that it is such an excellent pollinator attractant and may cause bees to swarm. Spraying it on pets controls insect issues as well. No other formula for flea or tick control is required, thereby allowing the pets to avoid treatment with costly and potentially harmful prescribed products. Treatment on household rugs will also remove fleas. One spray on a rug will treat the area for a month and the second spray a month later may be the last required. A single springtime application will refresh the treatment for the year.

In the bud finisher, the mixing of the oil and vinegar addition with the potassium bicarbonate creates carbon dioxide which is absorbed through the plant surface. Potassium bicarbonate leaves potassium residue when the carbon dioxide reaction is complete and the potassium is beneficial to the health of the plants. Potassium bicarbonate further control molds and fungus. Bicarbonates break down the negative charge on fungus and mold spores. Potassium is also released for the plant. This exposure to plants being treated enhances the positive effects of the present invention.

The minimum and maximum application rates call for diluting one portion of the invention as set out in the containers shown in FIGS. 1-4 and in ratios as detailed above into one gallon of water.

Figure 5:
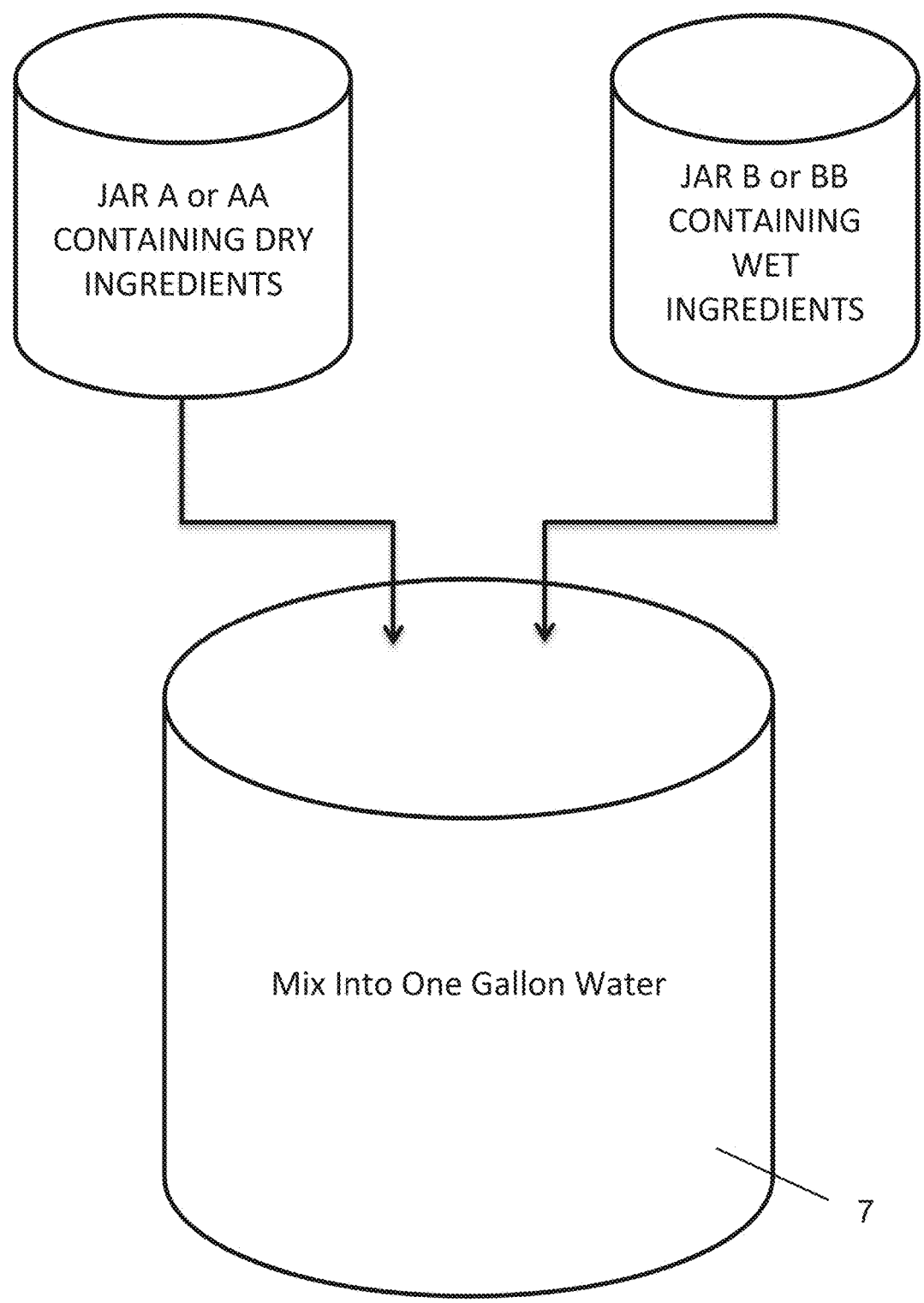
FIG. 5 is a schematic illustration of the bud finisher contents of Jar A and Jar B, or the bud shield ingredients in Jar AA and Jar BB, mixed into a third container of water.

No special protective gear is required for applying the formula on plants because the formula is no more toxic when sprayed on a plant than the native ingredients which are commonly found in a kitchen spice rack. After applying the present invention, new plant growth is observed as early as the next day. It never stops or slows down growth to work, unlike many pesticides which are known to slow down plant growth for ten to fourteen (10-14) days. Application may be made every one to seven (1-7) days, although it is even safe to spray it multiple times a day without slowing plant growth or harming it in any way. Testing has demonstrated that plants may be sprayed up to 28 times in 1 week without harm. The present invention works on contact, is absorbed quickly, and leaves a repellent effect in place even after rain. The dry ingredients of Jar A 1 and Jar AA 11 are routinely used as a dry rub on ribs, as dip with corn chips, or generally as a unique seasoning combination. The entire combined formula 7 shown in FIG. 5 can be poured upon a rack of ribs for marinating. The use of a single product as both a food spice packet (legal foodstuff) and as a pesticide was not believed to be possible prior to the present invention and in fact regulations do not contemplate such a possibility.

The total weight of the spices in the preferred formulation is 0.75 ounces to every gallon of water. Compared with prior patents, black pepper plays a minimal role in the present invention formula. While the bud finisher works best in the ranges listed, some effect would be noted in a wider range. For example, 5,000 heat units would be a very weak bud finisher, or 100,000 heat units would be a very rapid bud finisher to the point the plant is somewhat injured. That is what happened when unusually hot chili powder was put into the formula; it pushed the trichomes to amber in a single application, turned the pistils brown and turned the vegetative part of the flowers darker too. So, there is some comparable effect outside the preferred range. Higher than 100,000 heat units would start to head into the herbicide range and be potentially harmful to plants. In addition, these are the ranges for trichomes on the cannabis plant and the flowers/vegetables tested. With one-third of the plant realm possessing trichomes there could be plant/trichome varieties which respond better to very low or very high amounts of the formula, hence the potential usefulness in the range of 25%-200% of the preferred formulas. Other than relative to heat units, the bud finisher aspect of the present invention only really functions properly within the ranges listed in the preferred embodiment, but will function as a pesticide within at least double these ranges. With these options, matters of taste can be accommodated by tinkering with the spice recipe to explore the most desirable culinary flavors.

In the present invention the powdered ancho chili, oregano, cayenne, and cumin could be substituted with a more commonly referred to "chili powder." Additionally the coriander, cumin, turmeric, ginger, Fenugreek seeds, cinnamon, cloves, and nutmeg may be replaced with commercially available "curry powder." Early formulations of the present invention called for additional percentages of ingredients but are redundant with the grocery store spice mixes like curry and chili powder. While the refinements and specific ratios are demonstrated in the table and claimed herein, it may be that increased amounts of specific spices like turmeric may once again benefit the influence of the bud finisher and aspects of the pest deterrence. The preferred curry substitute to the individual ingredients is one marketed as Starwest Botanicals Organic.

Prior pesticide inventions claim a degree of control of about 55-65% but the present invention demonstrates a score much higher, with ranges of control well over 90%. Some tests have shown 100% effectiveness on multiple invasions or several different kinds of insects. It also provides the user with nearly total control of powdery mildew formation in a humid environment that endemically has a lot of powdery mildew around. In one six month study, powdery mildew has not been seen in six (6) months despite being pervasive through open air vents in the adjacent outdoor environment. Powdery mildew is not affecting plants inside or plants outside that are sprayed with bud finisher. A control group of plants and outdoor foliage with mites and other visible bugs have been overtaken by insects and powdery mildew while the sprayed group is flourishing. The use of the present invention allows gardening in areas where it would otherwise not be possible due to adverse climate conditions. The results of gardening with the benefit of the application of the present invention is so effective and needed that its use will revolutionize the industry and is vitally necessary.

The present invention enhances vitality of the plant and its products by performing a function usually performed by the sun with UV rays. Phenols and terpenes are created separately in the secretory glands at the base of the trichome head. Like UV rays, the present invention action causes them to mix and blend into cannabinoids in cannabis (or other essential oil compounds in other plants). Once combined these finished compounds are secreted into the top of the trichome head (the subcuticular oil storage cavity). The chemical reaction initiated by the application of the present formula mimics or replaces the sun's UV interaction with the trichome and finishes the trichome maturation process much more rapidly. The effect happens almost instantly, even when used in the dark, so light is not necessary for the maturation to occur. Terpenes are compounds which create the smell of a plant. The present invention greatly enhances scent and stabilizes it longer.

Some preliminary tests show the efficacy of the present invention as a ripening agent. When the inventor sprays one green tomato out of single bunch containing five tomatoes, the one sprayed turns to yellow or orange the next day and the non-sprayed ones stayed green. After 2 or 3 days of spraying, the sprayed tomato is fully ripe while the other, unsprayed tomatoes remain green. The present invention also creates fifty percent more (50%+) flowers on tomato plants which later turn into fruit. The present invention makes flowering sites proliferate on flowers and vegetables, speeds maturation of their fruit, enhances their scent and flavor, and holds them in full bloom longer.

The preferred and alternative formulas demonstrate a few, particularly 'ideal ranges', but the invention will have a wider range of possible variations which still would retain some level of efficacy. The ranges beyond those specifically set forth are disclosed herein and those ranges meet the objectives of the claimed invention. Some of the ingredients may be nothing more than a 'propellant packet' for the other ingredients.

This invention is new because there is nothing on the market which combines these elements for these specific purposes. There has never been a mixture that has efficacy as a pesticide but which is also edible and tastes good. A pesticide which is also a health tonic, bloom enhancer, pollinator attractant, and ripening agent is new. This product works against Japanese beetles which no other natural product currently does. Mixing two ingredients together at the point of use to create an extra release of carbon dioxide for consumer use is new. The invention is useful in that the spices are beneficial to human health if consumed on a sprayed product, so any residue would be beneficial. The product removes molds or soft bodied insects as well as Japanese beetles and forms a protective barrier against their return for seven to fourteen (7-14) days. The invention is non-obvious because using spices in powder form would be illogical. Oils are the standard. It would not be possible or suggested to mix together any combination of other products to arrive at this product and its effects, there is no antecedent or precursor to this formula. Spices are put through a silk screen filtering process, so they are different than they would be if found in nature or from a store shelf. This invention contains spices which are not currently used in any other pesticide product, nor found in this combination in any commercial spice packet. The synergy of the spices in exact proportion creates the claimed effects, this spice combo and proportion would be unprecedented from the pesticides before it and would not be discovered in a logical way.

The inventor tried all the home remedies and all the products available and they only last one to two (1-2) days in a heavily infected environment, whereas the present invention lasts three to fourteen (3-14) days and is exponentially more effective than the other natural cures which use similar or even some of the same spices in combination. The precision of the mixture in the exact proportions set forth in this invention creates a synergy for overall magnified efficacy. The addition of oil and vinegar is original and unexpected in this field and their addition brings the synergy into further balance. The carbon dioxide released from adding the vinegar is also of note. This exact proportional symmetry is completely unique and unexpected and could not have been uncovered by obvious or known mechanisms of research.

The synergy provides multiple functions from pesticide to pollinator attractant to bud finisher to a spice for a dinner salad. The other products don't claim such results. This invention will be taken to market with 100% natural, organic food-grade ingredients (such as spices and similar mixtures) that materially and dramatically benefit either people or plants. When diluted with water it is 100% safe-so safe it can literally serve to marinate a steak that would be delicious as a result. But when sprayed on plants according to the inventor's directions, it will:

End and thereafter prevent infestations by pests common to plants that produce fruit, vegetables and flowers. (The present invention is more effective than any "natural" product on the market—and for a longer list of pests than addressed by any other single product on the market.)

Cause plants to grow more vigorously, producing a greater number of flowers and fruits/vegetables than otherwise.

Greatly enhance the scent and flavor of flowers and fruits.

As needed or desired, incite grown fruits/vegetables and flowers to ripen and "finish" their blooming process, for some species saving weeks of growing time that would otherwise be needed.

It is further intended that any other embodiments of the present invention which result from any changes in application or method of use or operation, method of manufacture, shape, size, or material which are not specified within the detailed written description or illustrations contained herein yet are considered apparent or obvious to one skilled in the art are within the scope of the present invention.

I claim:

1. An edible, plant-treatment formulation for application onto a plant by a human, the formulation comprising:
   a first container having a combination of food grade products manufactured for human consumption, the combination comprising,
   one part Nutmeg powder,
   one part Oregano powder,
   one and one-half parts Fenugreek powder,
   three and one-half parts Cayenne powder and Cumin powder,
   seven parts Black Pepper powder, Ancho Chili powder and Coriander powder,
   fourteen and one-half parts Turmeric powder and Clove powder,
   twenty nine parts Garlic powder, Ginger powder and Cinnamon powder, and
   seventy-five parts Potassium Bicarbonate powder; and
   a second container comprising 150 parts Sesame Oil and 150 parts Apple Cider Vinegar,
   wherein all parts are parts by volume,
   and wherein the first and second containers are packaged together.

2. The edible, plant-treatment formulation of claim 1, wherein the formulation has a measured volume having a number of heat units in a range of 5,000-100,000 heat units.

3. The edible, plant-treatment formulation of claim 1, wherein the formulation has a measured volume having a number of heat units in a range of 30,000-50,000 heat units.

4. The edible, plant-treatment formulation of claim 1, wherein the formulation has a measured volume having a number of heat units for maturation of trichomes.

5. The edible, plant-treatment formulation of claim 1, wherein the formulation has a measured volume having a number of heat units for maturation of trichomes synchronously with maturation of the pistils of the plant.

6. A method of treating plants using the plant-treatment formulation of claim 1, wherein the formulation is diluted in water, added to a spray bottle and sprayed onto the plants and or soil near the plants.

7. A plant-treatment formulation with a measured volume comprising:
   Sesame Oil,
   Potassium Bicarbonate powder;
   Garlic powder,
   Ginger powder, Cinnamon powder,
Turmeric powder;
Clove powder,
Black Pepper powder,
Ancho Chili powder,
Coriander powder,
Cayenne powder,
Cumin powder,
Fenugreek powder,
Nutmeg powder, and
Oregano powder;
wherein the measured volume has a number of heat units in a range of 5,000-100,000 heat units,
wherein the measured volume comprises a plurality of concentration tiers,
wherein the plurality of concentration tiers have a relative proportionality as follows:
   a first tier comprising a Sesame Oil, the Sesame Oil having a specific volume,
   a second tier of Potassium Bicarbonate having a volume which is in a range of approximately one-half to two-thirds the specific volume of the Sesame Oil,
   a third tier having equal parts of Garlic powder, Ginger powder, and Cinnamon powder, the third tier having a volume less than the specific volume of the Sesame Oil,
   a fourth tier having equal parts of Turmeric powder and Clove powder, the fourth tier having a volume less than the volume of the third tier,
   a fifth tier having equal parts of Black Pepper powder, Ancho Chili powder, and Coriander powder, the fifth tier having a volume less than the volume of the fourth tier,
   a sixth tier having equal parts of Cayenne powder and Cumin powder, the sixth tier having a volume less than the volume of the fifth tier,
   a seventh tier of Fenugreek powder, the seventh tier having a volume less than the volume of the sixth tier, and
   an eighth tier of substantially equal parts of Nutmeg powder and Oregano powder, the eighth tier having a volume less than the volume of the seventh tier;
wherein the plurality of concentration tiers total 100% of the measured volume, and
wherein the formula can be diluted with water.

8. The plant treatment formulation of claim 7 further comprising Apple Cider Vinegar.

9. The plant treatment formulation of claim 7, wherein the first tier further comprises Apple Cider Vinegar having a specific volume approximately equal to the specific volume of the Sesame Oil.

10. An edible, plant-treatment formulation including a combination of ingredients comprising:
   a first quantity having a portion of Sesame Oil, wherein the first quantity makes up approximately 50% of the combination,
   a second quantity Potassium Bicarbonate powder, wherein the second quantity is one-quarter of the first quantity,
   a third quantity having equal portions of Garlic powder, Ginger powder, and Cinnamon powder, wherein the third quantity is less than the first quantity,
   a fourth quantity having equal portions of Turmeric powder and Clove powder, wherein the fourth quantity is less than the third quantity,
   a fifth quantity having equal portions of Black Pepper powder, Ancho Chili powder, and Coriander powder, wherein the fifth quantity is less than the fourth quantity,
   a sixth quantity having equal portions of Cayenne powder and Cumin powder, wherein the sixth quantity is less than the fifth quantity,
   a seventh quantity having a portion of Fenugreek powder, wherein the seventh quantity is less than the sixth quantity, and
   an eighth quantity having equal portions of Nutmeg powder and Oregano powder, wherein the eighth quantity is less than the seventh quantity.

11. The edible, plant-treatment formulation of claim 10, the combination of ingredients further comprising:
   the first quantity having equal portions of Sesame Oil and Apple Cider Vinegar.

12. A method of treating plants using the plant-treatment formulation of claim 10, wherein the formulation is diluted in water added to a spray bottle and sprayed onto the plants and or soil near the plants.

\* \* \* \* \*